US008679535B2

(12) United States Patent
Baichwal et al.

(10) Patent No.: US 8,679,535 B2
(45) Date of Patent: Mar. 25, 2014

(54) SUSTAINED RELEASE MATRIX SYSTEMS FOR HIGHLY SOLUBLE DRUGS

(75) Inventors: Anand R. Baichwal, Wappingers Falls, NY (US); Troy W. McCall, Germantown, TN (US); Lirong Liu, Washington Township, NJ (US); Steve Labudzinski, Poughkeepsie, NY (US)

(73) Assignee: Endo Pharmaceuticals Inc., Malvern, PA (US)

( * ) Notice: Subject to any disclaimer, the term of this patent is extended or adjusted under 35 U.S.C. 154(b) by 1260 days.

(21) Appl. No.: 11/729,024

(22) Filed: Mar. 27, 2007

(65) Prior Publication Data
US 2007/0218137 A1    Sep. 20, 2007

Related U.S. Application Data

(63) Continuation of application No. 10/740,213, filed on Dec. 18, 2003, now abandoned, which is a continuation of application No. 09/676,376, filed on Sep. 29, 2000, now abandoned.

(60) Provisional application No. 60/157,200, filed on Sep. 30, 1999.

(51) Int. Cl.
   *A61K 9/14*    (2006.01)
(52) U.S. Cl.
   USPC ........... 424/485; 424/484; 424/488; 424/464; 424/465; 424/468; 424/469
(58) Field of Classification Search
   USPC ........................................... 424/485
   See application file for complete search history.

(56) References Cited

U.S. PATENT DOCUMENTS

| | | | |
|---|---|---|---|
| 3,485,847 A | 12/1969 | Bossert, F. et al. | |
| 3,784,684 A | 1/1974 | Bossert, F. et al. | |
| 4,191,772 A | 3/1980 | Woog et al. | |
| 4,346,709 A | 8/1982 | Schmitt | |
| 4,412,986 A | 11/1983 | Kawata et al. | |
| 4,562,069 A | 12/1985 | Hegasy et al. | |
| 4,665,081 A | 5/1987 | Doi et al. | |
| 4,673,564 A | 6/1987 | Kawata et al. | |
| 4,696,815 A | 9/1987 | Schepky et al. | |
| 4,726,951 A | 2/1988 | Panoz et al. | |
| 4,764,382 A | 8/1988 | Kydonieus et al. | |
| 4,765,989 A | 8/1988 | Wong et al. | |
| 4,765,990 A | 8/1988 | Sugimoto et al. | |
| 4,792,448 A | 12/1988 | Ranade | |
| 4,792,450 A | 12/1988 | Kydonieus et al. | |
| 4,792,452 A | 12/1988 | Howard et al. | |
| 4,803,076 A | 2/1989 | Ranade | |
| 4,803,081 A | 2/1989 | Falk et al. | |
| 4,808,413 A | 2/1989 | Joshi et al. | |
| 4,851,229 A | 7/1989 | Magruder et al. | |
| 4,867,985 A | 9/1989 | Heafield et al. | |
| 4,880,623 A | 11/1989 | Piergiorgio et al. | |
| 4,889,723 A | 12/1989 | Kim et al. | |
| 4,892,741 A | 1/1990 | Ohm et al. | |
| 4,894,235 A | 1/1990 | Kohne et al. | |
| 4,904,699 A | 2/1990 | Bauer | |
| 4,940,587 A | 7/1990 | Jenkins et al. | |
| 4,942,040 A | 7/1990 | Ragnarsson et al. | |
| 4,973,469 A | 11/1990 | Mulligan et al. | |
| 4,983,593 A | 1/1991 | Miyajima et al. | |
| 4,994,276 A | 2/1991 | Baichwal et al. | |
| 5,007,790 A | 4/1991 | Shell | |
| 5,015,479 A | 5/1991 | Mulligan et al. | |
| 5,019,397 A | 5/1991 | Wong et al. | |
| 5,024,843 A | 6/1991 | Kuczynski et al. | |
| 5,051,262 A * | 9/1991 | Panoz et al. | 424/468 |
| 5,051,263 A | 9/1991 | Barry et al. | |
| 5,071,642 A | 12/1991 | Lahr et al. | |
| 5,091,190 A | 2/1992 | Kuczynski et al. | |
| 5,096,714 A | 3/1992 | Kuhrts | |
| 5,100,669 A | 3/1992 | Hyon et al. | |
| 5,108,757 A | 4/1992 | Erdos et al. | |
| 5,110,602 A | 5/1992 | Kim et al. | |
| 5,128,142 A | 7/1992 | Mulligan et al. | |
| 5,128,143 A | 7/1992 | Baichwal et al. | |
| 5,132,116 A | 7/1992 | Sournac et al. | |
| 5,133,974 A | 7/1992 | Paradissis et al. | |

(Continued)

FOREIGN PATENT DOCUMENTS

| | | |
|---|---|---|
| AU | 725494 | 10/2000 |
| CA | 2034096 | 7/1991 |

(Continued)

OTHER PUBLICATIONS

Khalifeh "Thermodynamic Evaluation of Ibuprofen Solubility in Aqueous and Non-Aqueous cosolvent systems", Dec. 2000 A Thesis submitted to the Faculty of Purdue University).*
Ghosh et al., Drug development and Industrial Pharmacy, 1998, 24(5), pp. 473-477.*
Database WPI Derwent Publications Ltd., London GB; AN 81-35085D XP002011749 and JP-A-56030485 (Sansho KK), 1981.
Cox, et al. "Development and Evaluation of a Multiple-Unit Oral Sustained Release Dosage Form for S(+)-ibuprofen: Preparation and Release Kinetics", *International J. of Pharmaceutics* (1999), 73-84.
Burgess, et al., "Spontaneous Formation of Small Sized Albumin/acacia Coacervate Particles", *J of Pharm. Pharmac.* (1993), 586-591.
Abstract XP-002326551; Nakamura, "Sustained-release gels containing plant gums and organic acid calcium salts," Chemical Abstract Service, Columbus, Ohio, U.S.; 1998.

(Continued)

*Primary Examiner* — James Rogers
(74) *Attorney, Agent, or Firm* — Davidson, Davidson & Kappel, LLC

(57) ABSTRACT

Disclosed are sustained release oral solid dosage forms comprising a therapeutically effective amount of a medicament having a solubility of more than about 10 g/l; a pH modifying agent; and a sustained release matrix comprising a gelling agent, said gelling agent comprising a heteropolysaccharide gum and a homopolysaccharide gum capable of cross-linking said heteropolysaccharide gum when exposed to an environmental fluid, said dosage form providing a sustained release of said medicament after oral administration to human patients.

19 Claims, 14 Drawing Sheets

(56) References Cited

U.S. PATENT DOCUMENTS

| | | | |
|---|---|---|---|
| 5,135,757 A | 8/1992 | Baichwal et al. | |
| 5,145,683 A | 9/1992 | Rhodes | |
| 5,160,734 A | 11/1992 | Ganesan et al. | |
| 5,169,638 A | 12/1992 | Dennis et al. | |
| 5,169,639 A | 12/1992 | Baichwal et al. | |
| 5,211,957 A | 5/1993 | Hagemann et al. | |
| 5,215,758 A | 6/1993 | Krishnamurthy | |
| 5,264,446 A | 11/1993 | Hegasy et al. | |
| 5,264,459 A | 11/1993 | Chelmicka-Schorr et al. | |
| 5,273,760 A | 12/1993 | Oshlack et al. | |
| 5,286,493 A | 2/1994 | Oshlack et al. | |
| 5,288,500 A * | 2/1994 | Ibsen | 424/489 |
| 5,292,534 A | 3/1994 | Valentine | |
| 5,330,761 A | 7/1994 | Baichwal | |
| 5,356,467 A | 10/1994 | Oshlack et al. | |
| 5,399,358 A | 3/1995 | Baichwal et al. | |
| 5,399,359 A * | 3/1995 | Baichwal | 424/464 |
| 5,399,362 A | 3/1995 | Baichwal et al. | |
| 5,415,871 A | 5/1995 | Pankhania et al. | |
| 5,439,687 A | 8/1995 | Compassi | |
| 5,455,046 A | 10/1995 | Baichwal | |
| 5,472,711 A | 12/1995 | Baichwal | |
| 5,476,654 A | 12/1995 | Conte et al. | |
| 5,478,574 A | 12/1995 | Baichwal et al. | |
| 5,512,297 A | 4/1996 | Baichwal | |
| 5,518,730 A | 5/1996 | Fuisz | |
| 5,525,351 A * | 6/1996 | Dam | 424/440 |
| 5,543,099 A | 8/1996 | Zhang et al. | |
| 5,554,387 A | 9/1996 | Baichwal | |
| 5,612,053 A | 3/1997 | Baichwal et al. | |
| 5,662,933 A | 9/1997 | Baichwal et al. | |
| 5,667,801 A | 9/1997 | Baichwal | |
| 5,670,168 A | 9/1997 | Baichwal et al. | |
| 5,738,865 A | 4/1998 | Baichwal et al. | |
| 5,773,025 A | 6/1998 | Baichwal | |
| 5,846,563 A | 12/1998 | Baichwal | |
| 5,958,456 A | 9/1999 | Baichwal et al. | |
| 6,039,980 A | 3/2000 | Baichwal | |
| 6,048,548 A | 4/2000 | Baichwal | |
| 6,056,977 A | 5/2000 | Bhagwat et al. | |
| 6,093,420 A | 7/2000 | Baichwal | |
| 6,093,424 A | 7/2000 | Han et al. | |
| 6,136,343 A | 10/2000 | Baichwal | |
| 6,245,355 B1 | 6/2001 | Baichwal | |
| 6,245,356 B1 | 6/2001 | Baichwal | |

FOREIGN PATENT DOCUMENTS

| | | |
|---|---|---|
| CA | 1288049 | 8/1991 |
| CA | 1313133 | 1/1993 |
| CA | 2101680 | 2/1994 |
| DE | 2714065 | 10/1978 |
| DE | 3400106 | 7/1985 |
| EP | 0147171 | 7/1985 |
| EP | 0234670 | 2/1987 |
| EP | 0218148 A1 | 4/1987 |
| EP | 0232155 | 8/1987 |
| EP | 0311582 A1 | 4/1989 |
| EP | 0311582 B1 | 4/1989 |
| EP | 0357793 | 3/1990 |
| EP | 0360562 A2 | 3/1990 |
| EP | 0581676 A2 | 2/1994 |
| EP | 0642785 A2 | 3/1995 |
| EP | 0047899 | 2/1996 |
| EP | 0722732 A1 | 7/1996 |
| EP | 0803255 A1 | 10/1997 |
| GB | 2160100 | 12/1995 |
| JP | 06009388 | 1/1994 |
| JP | 08099906 | 4/1996 |
| JP | 10236983 | 9/1998 |
| WO | 83/01570 | 5/1983 |
| WO | WO 8504100 | 9/1985 |
| WO | WO 89/02738 | 4/1989 |
| WO | WO 90/03165 | 4/1990 |
| WO | WO 92/06680 | 4/1992 |
| WO | WO 93/01803 | 2/1993 |
| WO | 93/13773 | 7/1993 |
| WO | WO 9423700 | 10/1994 |
| WO | 95/13055 | 5/1995 |
| WO | 95/23593 | 9/1995 |
| WO | 97/26865 A1 | 7/1997 |
| WO | 97/32584 | 9/1997 |
| WO | WO 9801117 A1 * | 1/1998 |

OTHER PUBLICATIONS

Supplementary Partial European Search Report issued in European Application No. 00968498; May 2005.
Chemical Abstracts, vol. 104 (1986) Abstract 174662y.
Chemical Abstracts, vol. 99 (1983) Abstract 128360d.
Chemical Abstracts, vol. 92 (1980) Abstract 135278s.
Chemical Abstracts, vol. 92 (1980) Abstract 82429h.
Chemical Abstracts, vol. 77 (1972) Abstract 39130g.
Chemical Abstracts, vol. 70 (1969) Abstract 17133p.
Chemical Abstracts, vol. 98 (1983) Abstract 221832y.
Alderman, D.A., "A review of cellulose ethers in hydrophilic matrices for oral controlled-release dosage forms", Int. J. Pharm. Tech & Prod. Mfg., vol. 5, pp. 1-9 (1984).
Haynes, R. Brian, M.D., et al., "Manipulation of the therapeutic regimen to improve compliance:Conceptions and misconceptions", Clinical Pharmacology and Therapeutics, vol. 22, No. 2, (Aug. 1977).
English translation of Japanese Patent Laid-Open-To-Public, publication No. 8/1986, publication date Jan. 6, 1986, JP Patent Application No. 118,789/1984; JP Patent Application date: Jun. 9, 1984.
Techniques of Solubilization of Drugs, edited by Samuel H. Yalkowsky, The Upjohn Company, pub. Marcel Dekker, Inc., New York and Basel, pp. 308-315 (1981).
"Crystallization and Granulation", Remington's Practice of Pharmacy, $9^{th}$ Ed. Chapter XXVII, pp. 208-211, 1950.
Ritschel, Angewandte Blopharmazie, pp. 293-302 (1973).
Sugimoto, I., et al., "Dissolution and Absorption of Nifedipine From Nifedipine-Polyvinylpyrrolidone Coprecipitate", Drug Development and Industrial Pharmacy, vol. 6, No. 2, pp. 137-161 (1980).
Kleinbloesem, M., et al., Nifedipine: Kinetics and dynamics in healthy subjects, Clin. Pharmacol. Ther., vol. 35, No. 6, pp. 742-749 (1984).
Raemsch, K, et al., "Pharmacokinetics and Metabolism of Nifediphine", Hypertension Supplement II, vol. 5, No. 4, Jul.-Aug. 18-24, 1983.
McGinity, J.W., et al ., "Dissolution and Uniformity Properties of Ordered Mixes of Micronized Griseofulvin and a Directly Compressible Excipient", Drug Development and Industrial Pharmacy, vol. 11, No. 4, pp. 891-900 (1985).
The Merck Index, pp. 848-849, $9^{th}$ Ed. (1976).
D.Q.M. Craig, "Polyethyelene Glycols and Drug Release", Drug Development and Industrial Pharmacy, 16(17), pp. 2501-2526 (1990).
Helbig, J. et al. "Pharmaceutical oral dosage forms of an active agent capable of forming or releasing bicarbonate ions", Pharmaceuticals, (Abstract-98:221837d), vol. 98, p. 63 (1983).
Derwent Abstract DE 3400106A, 1984.
Factors Affecting Prednisolone Release from Hydrogels Prepared with Water-Soluble Dietary Fibers, Xanthan and Locust Bean Gums, Kazunori et al., Chem. Pharm.Bull 40 (2), pp. 459-462 (1992).
Investigation and Rectal Absorption of Indomethacin from Sustained-Release Hydrogel Suppositories Prepared with Water Soluble Dietary Fibers, Xanthan Gum and Locust Bean Gum, Kazunori et al., Biol. Pharm. Bull 16(4), pp. 391-394 (1993).
Applicant's Response to Office Action dated Dec. 22, 2006 filed in corresponding U.S. Appl. No. 10/740,213.
Office Action dated Aug. 22, 2006 issued in corresponding U.S. Appl. No. 10/740,213.
Applicant's Response to Office Action dated Jul. 19, 2006 filed in corresponding U.S. Appl. No. 10/740,213.
Office Action dated Apr. 19, 2006 issued in corresponding U.S. Appl. No. 10/740,213.
Office Action dated Jun. 18, 2003 issued in corresponding U.S. Appl. No. 09/676,376.

(56) References Cited

OTHER PUBLICATIONS

Applicant's Response to Office Action dated Mar. 10, 2003 filed in corresponding U.S. Appl. No. 09/676,376.
Applicant's Response to Office Action dated Nov. 1, 2002 filed in corresponding U.S. Appl. No. 09/676,376.
Office Action dated Jul. 3, 2002 issued in corresponding U.S. Appl. No. 09/676,376.
Applicant's Response to Office Action dated Apr. 3, 2002 filed in corresponding U.S. Appl. No. 09/676,376.
Office Action dated Oct. 3, 2001 issued in corresponding U.S. Appl. No. 09/676,376.

* cited by examiner

SUSTAINED RELEASE MATRIX SYSTEMS FOR HIGHLY SOLUBLE DRUGS

This application claims the benefit of provisional application Ser. No. 60/157,200 filed Sep. 30, 1999, the disclosure of which is hereby incorporated by reference.

BACKGROUND OF THE INVENTION

The advantages of controlled release products are well known in the pharmaceutical field and include the ability to maintain a desired blood level of a medicament over a comparatively longer period of time while increasing patient compliance by reducing the number of administrations necessary to achieve the same. These advantages have been attained by a wide variety of methods. For example, different hydrogels have been described for use in controlled release medicines, some of which are synthetic, but most of which are semi-synthetic or of natural origin. A few contain both synthetic and non-synthetic material. However, some of the systems require special process and production equipment, and in addition some off these systems are susceptible to variable drug release.

Oral controlled release delivery systems should ideally be adaptable so that release rates and profiles can be matched to physiological and chronotherapeutic requirements.

For the most part, the release rate of oral delivery systems have been classified according to the mechanism of release, such as zero order, first order, second order, pseudo-first order, and the like, although many pharmaceutical compounds release medicament via other, complicated mechanisms.

First order mechanisms refer to situations where the reaction rate is dependent on the concentration of the reacting substance (and therefore is dependent on the first power of the reactant). In such mechanisms, the substance decomposes directly into one or more products.

Second order mechanisms occur when the experimentally determined rate of reaction is proportional to the concentration of each of two reactants, or to the second power of the concentration of one reactant.

Pseudo first order reactions are generally defined as second order reactions which behave as though they are governed by a first order mechanism, and occur, for example, when the amount of one reacting material is manipulated by being present in great excess or being maintained at a constant concentration as compared to the other substance. In such circumstances, the reaction rate is determined by the manipulated substance.

Zero order mechanisms refer to situations where the reaction rate is independent of the concentration of the reacting substance (and therefore is dependent on the zero power of the reactant), the limiting factor being something other than the concentration of the reacting substance (e.g., the medicament). The limiting factor in a zero order mechanism may be, for example, the solubility of the reacting substance or the light intensity in photo chemical reactions.

As previously mentioned, however, many chemical reactions are not simple reactions of zero-, first-, or second-order, and the like, and instead comprise a combination of two or more reactions.

Moreover, other factors may influence the reaction rate, including temperature, pH, food effect variability, ions and ionic strength dependency, viscosity dependency, corrosion/erosion variability, content uniformity problems, flow and weight uniformity problems, carrying capacity and mechanical strength problems, hydrolysis, photochemical decomposition, interaction between components (such as interactions between the drug and other ingredients in the formulation, such as buffers, preservatives, and the like), the concentration of solvents of low dielectric constant (when the reaction involves oppositely charged ions), etc.

While many controlled and sustained release formulations are already known, certain soluble to highly soluble drugs present formulation difficulties when included in such formulations. Sustained release formulations with soluble drugs are susceptible to "dose dumping". This occurrence is where the release of the active ingredient is delayed, but when release is initiated, the rate is extremely high. This elevated release rate is associated with blood plasma fluctuations which can possibly result in decreased therapeutic effect or increased toxicity. These are the same problems which sustained release formulations are supposed to solve.

Further, it is often not possible to readily predict whether a particular sustained release formulation will provide the desired sustained release for a soluble to highly soluble drug. It has generally been found that it is necessary to carry out considerable experimentation to obtain sustained release formulations providing the desired bioavailability of such drugs when ingested.

In order to compensate for the unpredictability associated with having a controlled release formulation provide the desired sustained release for a soluble to highly soluble drug, it is sometimes considered desirable to provide a formulation with bi-modal or multi-phasic kinetics. Bimodal or multi-phasic release may be characterized by an initial high rate followed by a slower rate as the dosage form passes the upper portion of the small intestine where absorption is maximum and finally another higher rate as the dosage form passes into the further end of the intestine where absorption is less than before.

Bimodal release is considered to be advantageous for a number of reasons, including but not limited to the fact that bimodal release allows the formulator to compensate for changing absorption rates of the medicament in the gastrointestinal tract by providing a rapid onset of action (when the formulation is located in the stomach) and compensate for relatively slow absorption by providing a relatively rapid release rate (e.g., when the formulation is located in the large intestine).

Bimodal release formulations have been provided in a number of different manners to date.

For example, International Publication Number WO/87/00044 describes therapeutic formulations which are said to have bimodal release characteristics. WO 87/00044 describes a carrier base material for therapeutically active medicaments in a solid dosage formulation that are said to produce a bimodal controlled release profile characterized by a rapid initial release of medicament followed by a substantially constant rate of release for a period of time, after which the release rate is greater than the constant rate previously observed. The carrier based material comprises bimodal hydroxypropylmethylcellulose ethers with a methoxy content of 19-30%, a hydroxy propoxy content of 4-12%, a viscosity of 40-19,000 cps, an average molecular weight of 20,000-140,000, and which demonstrates a bimodal release profile in accordance with an assay method described therein. The bimodal hydroxypropylmethylcelluloses comprise 5-99% by weight of the total formulation, depending upon the active ingredient and length of drug released desire.

A. C. Shah et al. "Gel-Matrix Systems Exhibiting Bimodal Controlled Release For Oral Drug Delivery", Journal of Controlled Release, 9(1989), pp. 169-175, further reported that certain "types" of hydroxypropylmethylcellulose ethers are found to display a bimodal drug release profile. However, in that study, series of hydroxypropylmethylcellulose ether polymers were found to provide bimodal and non-bimodal release profiles from polymer-drug matrix tablets, which results appeared to depend upon the supplier of the polymer (and therefore upon, e.g., the method of manufacture, ionic composition, variations in the distribution of substituent groups, or distribution of molecular weight fractions).

P. Giunchedi et al., "Ketoprofen Pulsatile Absorption From 'Multiple Unit' Hydrophilic Matrices" International Journal of Pharmaceutics, 77(1991), pp. 177-181 described an extended release oral formulation of Ketoprofen comprising a multiple unit formulation constituted by four hydrophilic matrices of identical composition, each containing 50 mg of drug and prepared with hydroxypropylmethylcellulose (Methocel®) and placed in a gelatin capsule. Pulsatile plasma levels (2 peaks at 2nd and 8th hours after-dosing) were said to be obtained, whereas in vitro tests resulted in a fairly constant drug release.

U. Conte et al., "A New Ibuprofen Pulsed Release Oral Dosage Form", Drug Development And Industrial Pharmacy, 15(14-16), pp 2583-2596 (1989) reported that a pulsed released pattern was obtained from a 3-layer tablet wherein two layers contained a dose of drug, and an intermediate layer acted as a control element separating the drug layers. The control element was a mixture of water-swellable polymers (hydroxypropylmethylcelluloses). An outer film of an impermeable polymer coated the tablet. A superdisintegrant (sodium starch glycolate and cross-linked polyvinyl pyrrolidone) was included in the drug layers.

K. A. Kahn et al, "Pharmaceutical Aspects And In-Vivo Performance Of Brufen Retard—An Ibuprofen SR Matrix Tablet", Proced. Intern. Symp. Control. Rel. Bioact. Mater., 18(1991), Controlled Release Society, Inc., describes a formulation containing 800 mg of ibuprofen which is said to provide a bimodal release pattern. The release retarding agent utilized therein was xanthan gum. The ingredients were blended to the appropriate xanthan gum content, and thereafter compressed into tablets and film coated. The amount of xanthan gum included inversely affected the rate of drug release. An increase in drug particle size or quantity of filmcoat per tablet did not significantly effect the rate of drug release. Although an increase in particle size of the xanthan gum caused a more pronounced burst effect, the application of the film-coat overcame this burst effect. The rapid initial release of the medicament was hypothesized to be related to changes in the formation of the gel layer, wherein larger particles gel more slowly and are sloughed off before a coherent matrix can form.

In our U.S. Pat. Nos. 4,994,276, 5,128,143, and 5,135,757, hereby incorporated by reference, we reported that a controlled release excipient which is comprised of synergistic heterodisperse polysaccharides (e.g., a heteropolysaccharide such as xanthan gum in combination with a polysaccharide gum capable of cross-linking with the heteropolysaccharide, such as locust bean gum) is capable of processing into oral solid dosage forms using either direct compression, following addition of drug and lubricant powder, conventional wet granulation, or a combination of the two. The release of the medicament from the formulations therein proceeded according to zero-order or first-order mechanisms.

Our own U.S. Pat. Nos. 5,472,711 and 5,478,574, hereby incorporated by reference, we report a formulation capable of providing multi-phasic or bi-phasic controlled release of a therapeutically active medicament in vitro by incorporating an effective amount of a pharmaceutically acceptable surfactant with the above-referenced excipient.

An example of a highly soluble drug used in the present invention is diltiazem, which is a benzothiazine derivative possessing calcium antagonist activity. Diltiazem is widely used in the treatment of hypertension and angina. Accordingly, a great deal of attention has been given to the preparation of sustained release diltiazem which provides an acceptable release profile. For example U.S. Pat. Nos. 4,894,240 and 5,364,620 (Geoghegan, et al.) describe a diltiazem pellet formulation suitable for once daily administration. This formulation comprises a diltiazem core in association with an organic acid, surrounded by an insoluble multi-layer membrane. The membrane allows the release of diltiazem from the pellet at a rate allowing controlled absorption over a 24 hour period following administration.

Other techniques have been described in the prior art for preparing sustained release diltiazem formulations. For example, U.S. Pat. No. 5,419,917 (Chen et al.) describes a composition which controls the rate of release of diltiazem from a hydrogel using a pharmaceutically effective ionizable compound.

Another example of a highly soluble drug used in the present invention is oxybutynin. Oxybutynin is widely used in the treatment of urological disorders, e.g., hyperactive bladder. Our own U.S. Pat. No. 5,399,359 discloses an oxybutynin sustained release formulation comprising a pharmaceutically effective amount of oxybutynin dispersed within a sustained release matrix comprising a gelling agent, an effective amount of a pharmaceutically acceptable water-soluble cationic cross-linking agent which cross-links with the gelling agent when the formulation is exposed to an environmental fluid, e.g., gastrointestinal fluid, and an inert diluent.

OBJECTS AND SUMMARY OF THE INVENTION

It is an object of the present invention to provide a bioavailable sustained release formulation for soluble to highly soluble therapeutically active medicaments.

It is a further object of the present invention to provide a formulation which can provide multi-phasic or bi-phasic controlled release for soluble to highly soluble medicaments.

It is a further object of the present invention to provide a method for preparing a bioavailable sustained release formulation for soluble to highly soluble therapeutically active medicaments.

It is yet another object of the present invention to provide a sustained release matrix which may be used in the preparation of a sustained release oral solid dosage form of soluble to highly soluble therapeutically active medicaments.

It is a further object of the present invention to provide a sustained release matrix which is suitable for providing, when combined with a medicament, a sustained release formulation which provides therapeutically effective blood levels of the medicament for e.g., 12 or 24 hours.

It is a further object of the invention to provide a diltiazem sustained release matrix formulation which provides a plasma profile similar to commercially available sustained release formulations, e.g., Cardizem CD.

It is a further object of the invention to provide a oxybutynin sustained release matrix formulation which provides a plasma profile similar to commercially available sustained release formulations, e.g., Ditropan XL.

The above-mentioned objects and others are achieved by virtue of the present invention, which relates in part to the surprising discovery that the incorporation of a pH modifying agent into a dosage form comprising a gelling agent, facilitates the release of the drug from the dosage form and provides a high bioavailability.

In certain embodiments, the sustained release oral solid dosage form comprises a therapeutically effective amount of a medicament having a solubility of more than about 10 g/l; a pH modifying agent; and a sustained release matrix comprising a gelling agent, the gelling agent comprising a heteropolysaccharide gum and a homopolysaccharide gum capable of cross-linking the heteropolysaccharide gum when exposed to an environmental fluid. Preferably, the dosage form provides a sustained release of the medicament for at least about 12 hours, preferably at least about 24 hours.

In certain embodiments, the dosage form further comprises a) a pharmaceutically acceptable surfactant which can provide a multi-phasic release of the drug; b) an inert diluent selected from, e.g., a monosaccharide, a disaccharide, a polyhydric alcohol, or mixtures thereof; c) a hydrophobic material to slow the hydration of the gelling agent; and/or d) an effective amount of a pharmaceutically acceptable ionizable gel strength enhancing agent suitable for modifying the release rate from the gel which is formed when the controlled release formulation is exposed to an environmental fluid. In a preferred embodiment, the formulation of the present invention comprises a tablet.

In a preferred embodiment of the invention, the ratio of medicament to gelling agent is preferably from about 10:1 to about 1:10, more-more preferably from about 5:1 to about 1:5, and most preferably from about 1.25:1 to about 2:1.

The present invention is also related to a method for providing a sustained release formulation of a medicament having high solubility in water, comprising preparing a matrix comprising a gelling agent comprising a heteropolysaccharide gum and a homopolysaccharide gum capable of crosslinking said heteropolysaccharide gum when exposed to an environmental fluid; an optional ionizable gel strength enhancing agent, an optionally inert pharmaceutical diluent; and an optional hydrophobic material, and thereafter adding a soluble to highly soluble medicament, a pH modifying agent and an optional pharmaceutically acceptable surfactant. Thereafter the resulting mixture is tableted such that a product is obtained having a ratio of medicament to gelling agent from about 10:1 to about 1:10, more preferably from about 5:1 to about 1:5, and most preferably from about 1.25:1 to about 2:1, such that a gel matrix is created when the tablet is exposed to an environmental fluid and such that the tablets each contain a therapeutically effective amount of the medicament. The resulting tablet provides therapeutically effective blood levels of the medicament for at least about 12 hours, and preferably about 24 hours.

The present invention is further related to a method of treating a patient by orally administering an oral solid dosage form as set forth above.

In certain preferred embodiments of the invention, the matrix can be prepared from a pre-granulated sustained release excipient comprising, e.g. from about 10 to about 99% by weight of a gelling agent, from about 0 to about 20% by weight of an ionizable gel strength enhancing agent, from about 1 to about 89% by weight of an inert pharmaceutical diluent, and from about 1 to about 20% of a hydrophobic material.

In other preferred embodiments the mixture of the matrix and inert diluent are granulated before the addition of the medicament, with a dispersion or solution of the hydrophobic material in an amount sufficient to slow the hydration of the matrix without disrupting the same.

In other preferred embodiments of the invention, a first portion of the medicament is introduced during the granulation of the excipient, and a second portion of the drug is introduced extragranularly, or after the granulation step. Such an embodiment provides an initial rapid release of the medicament.

In preferred embodiments, the medicament is highly soluble, i.e., has a solubility of more than about 100 g/l.

In other preferred embodiment, the medicament comprises a calcium channel blocker, preferably a benzothiazine, most preferably diltiazem or a pharmaceutically acceptable salt thereof.

In other preferred embodiments, the medicament comprises an antispasmodic, preferably oxybutynin or a pharmaceutically acceptable salt thereof.

By "sustained release" it is meant for purposes of the present invention that the therapeutically active medicament is released from the formulation at a controlled rate such that therapeutically beneficial blood levels (but below toxic levels) of the medicament are maintained over an extended period of time, e.g., at least about 12 hour or at least about 24 hours.

By "bioavailable" it is meant for purposes of the present invention that the therapeutically active medicament is absorbed from the sustained release formulation and becomes available in the body at the intended site of drug action, preferably within 80% of a reference standard (based on comparison of the AUC).

By "soluble", it is meant that the therapeutically active medicament has an aqueous solubility of more than about 10 grams per liter (g/l).

By "highly soluble"; it is meant that the therapeutically active medicament has an aqueous solubility of more than about 100 grams per liter (g/l).

The term "environmental fluid" is meant for purposes of the present invention to encompass, e.g., an aqueous solution, or gastrointestinal fluid.

The term "pH modifying agent" is meant for purposes of the present invention to mean any substance which decreases the ionization of the medicament, whereby the release of the drug from the hydrogel matrix and into solution is facilitated.

The term "Cmax" is meant for purposes of the present invention to mean then maximum plasma concentration of a medicament achieved after administration of a dosage form in accordance with the invention.

The term "Tmax" is meant for purposes of the present invention to mean the elapsed time from administration of a dosage form to the time the Cmax of the medicament is achieved The term "$W_{50}$" is meant for purposes of the present invention to mean the time period measured by the width of the plasma concentration curve at 50% of the height of the Cmax.

For purposes of the present invention, the dosage form can have bi-modal kinetics, and accordingly, there can be multiple Cmaxs, Tmaxs and $W_{50}$s for the disclosed dosage forms.

BRIEF DESCRIPTION OF THE DRAWINGS

The following drawings are illustrative of embodiments of the invention and are not meant to limit the scope of the invention as encompassed by the claims.

DETAILED DESCRIPTION

Figure 1:
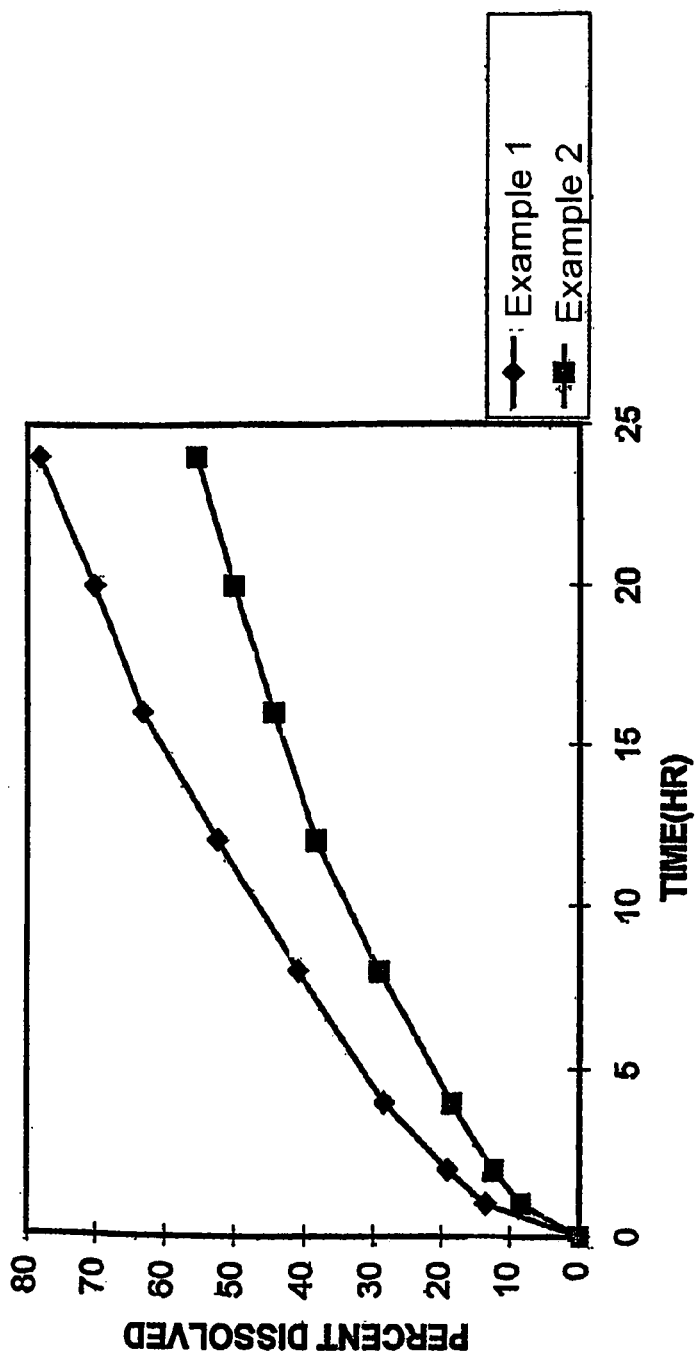
FIG. 1 is a graphical representation of the dissolution (mean percent dissolved over time) for Examples 1 and 2.

The sustained release matrix of the present invention can be a heterodisperse excipient (as previously reported in our U.S. Pat. Nos. 4,994,276, 5,128,143, and 5,135,757) which can comprise a gelling agent of both hetero- and homopolysaccharides which exhibit synergism, e.g., the combination of two or more polysaccharide gums produce a higher viscosity and faster hydration than that which would be expected by either of the gums alone, the resultant gel being faster-forming and more rigid.

The term "heteropolysaccharide" as used in the present invention is defined as a water-soluble polysaccharide containing two or more kinds of sugar units, the heteropolysaccharide having a branched or helical configuration, and having excellent water-wicking properties and immense thickening properties.

An especially preferred heteropolysaccharide is xanthan gum, which is a high molecular weight ($>10^6$) heteropolysaccharide. Other preferred heteropolysaccharides include derivatives of xanthan gum, such as deacylated xanthan gum, the carboxymethyl ether, and the propylene glycol ester.

The homopolysaccharide gums used in the present invention which are capable of cross-linking with the heteropolysaccharide include the galactomannans, i.e., polysaccharides which are composed solely of mannose and galactose. Galactomannans which have higher proportions of unsubstituted mannose regions have been found to achieve more interaction with the heteropolysaccharide. Locust bean gum, which has a higher ratio of mannose to the galactose, is especially preferred as compared to other galactomannans such as guar and hydroxypropyl guar.

The controlled release properties of the controlled release formulations of the present invention may be optimized when the ratio of heteropolysaccharide gum to homopolysaccharide material is about 1:1.5, although heteropolysaccharide gum in an amount of from about 10 to about 90 percent or more by weight of the heterodisperse polysaccharide material provides an acceptable slow release product. The combination of any homopolysaccharide gums known to produce a synergistic effect when exposed to aqueous solutions may be used in accordance with the present invention. It is also possible that the type of synergism which is present with regard to the gum combination of the present invention could also occur between two homogeneous or two heteropolysaccharides. Other acceptable gelling agents which may be used in the present invention include those gelling agents well-known in the art. Examples include vegetable gums such as alginates, carrageenan, pectin, guar gum, modified starch, hydroxypropylmethylcellulose, methylcellulose, and other cellulosic materials such as sodium carboxymethylcellulose and hydroxypropyl cellulose. This list is not meant to be exclusive.

The inert diluent of the sustained release excipient preferably comprises a pharmaceutically acceptable saccharide, including a monosaccharide, a disaccharide, or a polyhydric alcohol, and/or mixtures of any of the foregoing. Examples of suitable inert pharmaceutical fillers include sucrose, dextrose, lactose, microcrystalline cellulose, fructose, xylitol, sorbitol, starches, mixtures thereof and the like. However, it is preferred that a soluble pharmaceutical filler such as lactose, dextrose, sucrose, or mixtures thereof be used. The inert diluent or filler may alternatively comprise a pre-manufactured direct compression diluent as set forth below.

For example, it is possible to dry mix the ingredients of the sustained release excipient without utilizing a wet granulation step. This procedure may be utilized, for example, where a wet granulation is to be accomplished when the active ingredient is directly added to the ingredients of the sustained release excipient. On the other hand, this procedure may also be used where no wet granulation step whatsoever is contemplated. If the mixture is to be manufactured without a wet granulation step, and the final mixture is to be tableted, it is preferred that all or part of the inert diluent comprise a pre-manufactured direct compression diluent. Such direct compression diluents are widely used in the pharmaceutical arts, and may be obtained from a wide variety of commercial sources. Examples of such pre-manufactured direct compression excipients include Emcocel® (microcrystalline cellulose, N.F.), Emdex® (dextrates, N.F.), and Tab-Fine® (a number of direct-compression sugars including sucrose, fructose and dextrose), all of which are commercially available from Penwest Pharmaceuticals Co., Patterson, N.Y.). Other direct compression diluents include Anhydrous lactose (Lactose N.F., anhydrous direct tableting) from Sheffield Chemical, Union, N.J. 07083; Elcems® G-250 (powdered cellulose), N.F.) from Degussa, D-600 Frankur (Main) Germany; Fast-Flo Lactose® (Lactose, N.F., spray dried) from Foremost Whey Products, Banaboo, Wis. 53913; Maltrin® (Agglomerated maltodextrin) from Grain Processing Corp., Muscatine, Iowa 52761; Neosorb 60® (Sorbitol, N.F., direct-compression from Roquet Corp., 645 5th Ave., New York, N.Y. 10022; Nu-Tab® (Compressible sugar, N.F.) from Ingredient Technology, Inc., Pennsauken, N.J. 08110; Polyplasdone XL® (Crospovidone, N.F., cross-linked polyvinylpyrrolidone) from GAF Corp., New York, N.Y. 10020; Primojel® (Sodium starch glycolate, N.F., carboxymethyl starch) from Generichem Corp., Little Falls, N.J. 07424; Solka Floc® (Cellulose floc) from Penwest Pharmaceuticals Co., Patterson, N.Y. 10512; Spray-dried Lactose® (Lactose N.F., spray dried) from Foremost Whey Products, Baraboo, Wis. 53913 and DMV Corp., Vehgel, Holland; and Sta-Rx 15000® (Starch 1500) (Pregelatinized starch, N.F., compressible) from Colorcon, Inc., West Point, Pa. 19486.

In general, the formulation may be prepared as a directly compressible diluent, for example, by wet granulating, spray drying lactose or as a premixed direct compression diluent by art known methods. For purposes of the present invention, these specially treated inert diluents will be referred to as "directly compressible" inert diluents.

In certain embodiments, the ingredients of the sustained release excipient can be pre-manufactured. However, in other embodiments the active drug can be added to the excipient ingredients and that mixture melt granulated to form a granulation. Finally, where a surfactant is used, the surfactant comprising the solubilized or dispersed diltiazem or oxybutynin can be added directly to the mixture of ingredients.

In further embodiments of the present invention, the directly compressible inert diluent which is used in conjunction with the sustained release pharmaceutical excipient of the present invention is an augmented microcrystalline cellulose as disclosed in U.S. patent application Ser. No. 08/370,576, filed Jan. 9, 1995, and entitled "PHARMACEUTICAL EXCIPIENT HAVING IMPROVED COMPRESSIBILITY", by J. Staniforth, B. Sherwood and E. Hunter, hereby incorporated by reference in its entirety. The augmented microcrystalline cellulose described therein is commercially available under the tradename "Prosolv" from Penwest Pharmaceuticals Co.

An effective amount of a pharmaceutically acceptable surfactant can also be added to the above-mentioned ingredients of the excipient, or added at the time the medicament is added, in order to increase the bioavailability of the medicament. An example of a suitable surfactant is docusate sodium in an amount up to about 15% by weight of the solid dosage form. An especially preferred surfactant is sodium lauryl sulfate in an amount up to about 15% by weight of the solid dosage form.

In one embodiment, the surfactant is dissolved in a suitable solvent such as water, and is thereafter added to the blended mixture of the sustained release excipient and the medicament. This allows the surfactant to wet the particles of the excipient such that when the solvent evaporates the particles of the medicament which precipitate are tiny and do not aggregate. A granulate of the medicament and the surfactant is obtained which is preferably finely and homogeneously dispersed in the excipient.

In certain embodiments of the present invention, e.g. wherein the medicament is diltiazem or oxybutynin, the surfactant is included in an amount e.g., from about 1% to about 5%, or from about 1% to about 15% of the final product, by weight. However, the upper limit of surfactant included can be higher than 15%. One limiting factor is that the final product should provide a pharmaceutically acceptable formulation. For example, in the case of tablets, the upper limit of the amount of surfactant included is determined by the production of a pharmaceutically acceptable tablet, e.g., a tablet which has a friability of less than about 1% and a hardness of 6-8 kg.

The surfactants which may be used in the present invention generally include pharmaceutically acceptable anionic surfactants, cationic surfactants, amphoteric (amphipathic/amphophilic) surfactants, and non-ionic surfactants. Suitable pharmaceutically acceptable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates (including sodium lauryl sulfate (SLS)), ethoxylated alkyl sulfates, ester linked sulfonates (including docusate sodium or dioctyl sodium succinate (DSS)), alpha olefin sulfonates, and phosphated ethoxylated alcohols.

Suitable pharmaceutically acceptable cationic surfactants include, for example, monoalkyl quaternary ammonium salts, dialkyl quaternary ammonium compounds, amidoamines, and aminimides.

Suitable pharmaceutically acceptable amphoteric (amphipathic/amphophilic) surfactants, include, for example, N-substituted alkyl amides, N-alkyl betaines, sulfobetaines, and N-alkyl β-aminoproprionatess.

Other suitable surfactants for use in conjunction with the present invention include polyethyleneglycols as esters or ethers. Examples include polyethoxylated castor oil, polyethoxylated hydrogenated castor oil, polyethoxylated fatty acid from castor oil or polyethoxylated fatty acid from castor oil or polyethoxylated fatty acid from hydrogenated castor oil. Commercially available surfactants which can be used are known under trade names Cremophor, Myrj, Polyoxyl 40 stearate, Emerest 2675, Lipal 395 and PEG 3350.

The pH modifying agent facilitates the release of the drug from the matrix and is present from about 1% to about 50%; from about 1% to about 25% from about 1% to about 15%; or from about 1% to about 10% by weight of the final dosage form. In preferred embodiments, the pH modifying agent is an organic acid such as citric acid, succinic acid, fumaric acid, malic acid, maleic acid, glutaric acid or lactic acid.

The ionizable gel strength enhancing agent which is optionally used in conjunction with the present invention may be monovalent or multivalent metal cations. The preferred salts are the inorganic salts, including various alkali metal and/or alkaline earth metal sulfates, chlorides, borates, bromides, citrates, acetates, lactates, etc. Specific examples of suitable ionizable gel strength enhancing agent include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. Multivalent metal cations may also be utilized. However, the preferred ionizable gel strength enhancing agent are bivalent. Particularly preferred salts are calcium sulfate and sodium chloride. The ionizable gel strength enhancing agent of the present invention are added in an amount effective to obtain a desirable increased gel strength due to the cross-linking of the gelling agent (e.g., the heteropolysaccharide and homopolysaccharide gums). In alternate embodiments, the ionizable gel strength enhancing agent is included in the sustained release excipient of the present invention in an amount from about 1 to about 20% by weight of the sustained release excipient, and in an amount 0.5% to about 16% by weight of the final dosage form.

In certain embodiments of the present invention, the sustained release matrix of the present invention comprises a sustained release excipient which comprises from about 10 to about 99 percent by weight of a gelling agent comprising a heteropolysaccharide gum and a homopolysaccharide gum, from about 0 to about 20 percent by weight of an ionizable gel strength enhancing agent, and from about 1 to about 89 percent by weight of an inert pharmaceutical diluent. In other embodiments, the sustained release excipient comprises from about 10 to about 75 percent gelling agent, from about 2 to about 15 percent ionizable gel strength enhancing agent, and from about 30 to about 75 percent inert diluent In yet other embodiments, the sustained release excipient comprises from about 30 to about 75 percent gelling agent, from about 5 to about 10 percent ionizable gel strength enhancing agent, and from about 15 to about 65 percent inert diluent.

The sustained release excipient of the present invention (with or without the optional ionizable gel strength enhancing agent) may be further modified by incorporation of a hydrophobic material which slows the hydration of the gums without disrupting the hydrophilic matrix. This is accomplished in alternate embodiments of the present invention by granulating the sustained release excipient with the solution or dispersion of a hydrophobic material prior to the incorporation of the medicament. The hydrophobic polymer may be selected from an alkylcellulose such as ethylcellulose, other hydrophobic cellulosic materials, polymers or copolymers derived from acrylic or methacrylic acid esters, copolymers of acrylic and methacrylic acid esters, zein, waxes, shellac, hydrogenated vegetable oils, and any other pharmaceutically acceptable hydrophobic material known to those skilled in the art. The amount of hydrophobic material incorporated into the sustained release excipient is that which is effective to slow the hydration of the gums without disrupting the hydrophilic matrix formed upon exposure to an environmental fluid. In certain preferred embodiments of the present invention, the hydrophobic material is included in the sustained release excipient in an amount from about 1 to about 20 percent by weight. The solvent for the hydrophobic material may be an aqueous or organic solvent, or mixtures thereof.

In embodiments where the sustained release excipient of the present invention has been pre-manufactured, it is then possible to blend the same with the medicament, e.g., in a high shear mixer. In certain especially preferred embodiments, the medicament is a therapeutically effective benzothiazine which are useful for the treatment of circulatory disorders and high blood pressure. An especially preferred dihydropyridine is diltiazem. Useful formulations of diltiazem generally contain daily doses from about 30 to about 500 mg, preferably from about 120 mg to about 480 mg. In certain preferred embodiments of the present invention, the dosage form includes a dosage of diltiazem in an amount of 120 mg, 180 mg, 240 mg, or 300 mg for 24 hour formulations; and a dosage of diltiazem in an amount of 60 mg, 90 mg and 120 mg for 12 hour formulations.

In certain other especially preferred embodiments, then medicament is oxybutynin which is useful for the treatment of urological disorders. Useful formulations of oxybutynin generally contain daily doses from about 2.5 mg to about 50 mg, e.g., from about 2.5 mg to about 25 mg for 12 hour formulations and from about 5 mg to about 50 mg for 24 hour formulations. In certain preferred embodiments of the present invention, the dosage form includes a dosage of oxybutynin in an amount of 5 mg, 10 mg, or 15 mg for 24 hour formulations.

An effective amount of any generally accepted pharmaceutical lubricant, including calcium or magnesium soaps is preferably added to the mixture of ingredients (including medicament) prior to compression of the mixture into oral solid dosage forms, such as tablets. An example of a suitable lubricant is magnesium stearate in an amount of about 0.5 to about 3% by weight of the solid dosage form. An especially preferred lubricant is sodium stearyl fumarate, NF, commercially available under the trade name Pruv® from Penwest Pharmaceuticals Co.

The sustained release excipients of the present invention have uniform packing characteristics over a range of different particle size distributions and are capable of processing into the final dosage form (e.g., tablets) using either direct compression, following addition of drug and lubricant powder, or conventional wet granulation.

The properties and characteristics of a specific excipient system prepared according to the present invention is dependent in part on the individual characteristics of the homo and heteropolysaccharide constituents, in terms of polymer solubility, glass transition temperatures etc., as well as on the synergism both between different homo- and heteropolysaccharides and between the homo and heteropolysaccharides and the inert saccharide constituent(s) in modifying dissolution fluid-excipient interactions.

The combination of the gelling agent (i.e., a mixture of xanthan gum and locust bean gum) with the inert diluent, with or without the ionizable gel strength enhancing agent and hydrophobic polymer, provides a ready-to-use sustained release excipient product in which a formulator need only blend the desired active medicament, the pH modifying agent, the surfactant and an optional lubricant with the excipient before compressing the mixture to form slow release tablets. The excipient may comprise a physical admix of the gums along with a soluble excipient such as compressible sucrose, lactose or dextrose, although it is preferred to granulate or agglomerate the gums with plain (i.e., crystalline) sucrose, lactose, dextrose, etc., to form an excipient. The granulate form has certain advantages including the fact that it can be optimized for flow and compressibility; it can be tableted, formulated in a capsule, extruded and spheronized with an active medicament to form pellets, etc.

The pharmaceutical excipients prepared in accordance with the present invention may be prepared according to any agglomeration technique to yield an acceptable excipient product. In wet granulation techniques, the desired amounts of the heteropolysaccharide gum, the homopolysaccharide gum, and the inert diluent are mixed together and thereafter a moistening agent such as water, propylene glycol, glycerol, alcohol or the like is added to prepare a moistened mass. Next, the moistened mass is dried. The dried mass is then milled with conventional equipment into granules. Therefore, the excipient product is ready to use.

The pre-manufactured sustained release excipient is preferably free-flowing and directly compressible. Accordingly, the excipient may be mixed in the desired proportion with a therapeutically active medicament and optional lubricant (dry granulation). Alternatively, all or part of the excipient may be subjected to a wet granulation with the active ingredient and thereafter tableted. When the final product to be manufactured is tablets, the complete mixture, in an amount sufficient to make a uniform batch of tablets, is then subjected to tableting in a conventional production scale tableting machine at normal compression pressure, i.e. about 2000-1600 lbs/sq in. However, the mixture should not be compressed to such a degree that there is subsequent difficulty in its hydration when exposed to gastric fluid.

One of the limitations of direct compression as a method of tablet manufacture is the size of the tablet. If the amount of active is high a pharmaceutical formulator may choose to wet granulate the active with other excipients to attain a decent size tablet with the right compact strength. Usually the amount of filler/binder or excipients needed in wet granulation is less than that in direct compression since the process of wet granulation contributes to some extent toward the desired physical properties of a tablet.

When the medicament is diltiazem, the average tablet size for round tablets is preferably about 300 mg to 750 mg and for capsule-shaped tablets about 700 mg to 1000 mg.

The average particle size of the granulated excipient of the present invention preferably ranges from about 50 microns to about 400 microns and preferably from about 185 microns to about 265 microns. The particle size of the granulation is not narrowly critical, the important parameter being that the average particle size of the granules, must permit the formation of a directly compressible excipient which forms pharmaceutically acceptable tablets. The desired tap and bulk densities of the granulation of the present invention are normally between from about 0.3 to about 0.8 g/ml, with an average density of from about 0.5 to about 0.7 g/ml. For best results, the tablets formed from the granulations of the present invention are from about 5 to about 20 kg hardness. The average flow of the granulations prepared in accordance with the present invention are preferably from about 25 to about 40 g/sec. Tablets compacted using an instrumented rotary tablet-machine have been found to possess strength profiles which are largely independent of the inert saccharide component. Scanning electron photomicrographs of largely tablet surfaces have provided qualitative evidence of extensive plastic deformation on compaction, both at the tablet surface and across the fracture surface, and also show evidence of surface pores through which initial solvent ingress and solution egress may occur.

In certain embodiments of the invention, the tablet is coated with a sufficient amount of a hydrophobic polymer to render the formulation capable of further modifying the release of the medicament. The hydrophobic polymer which is included in the tablet coating may be the same or different material as compared to the hydrophobic polymeric material which is optionally granulated with the sustained release excipient.

In other embodiments of the present invention, the tablet coating may comprise an enteric coating material in addition to or instead of the hydrophobic polymer coating. Examples of suitable enteric polymers include cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. An example of a suitable commercially available enteric material is available under the trade name Eudragit™ L30D55.

In further embodiments, the dosage form may be coated with a hydrophilic coating in addition to or instead of the above-mentioned coatings. An example of a suitable material which may be used for such a hydrophilic coating is hydroxypropylmethyl-cellulose (e.g., Opadry® commercially available from Colorcon, West Point, Pa.).

The coatings may be applied in any pharmaceutically acceptable manner known to those skilled in the art. For example, in one embodiment, the coating is applied via a fluidized bed or in a coating pan. For example, the coated tablets may be dried, e.g., at about 60-70° C. for about 3-4 hours in a coating pan. The solvent for the hydrophobic polymer or enteric coating may be organic, aqueous, or a mixture of an organic and an aqueous solvent. The organic solvents may be, e.g., isopropyl alcohol, ethanol, and the like, with or without water.

In additional embodiments of the present invention, a support platform is applied to the tablets manufactured in accordance with the present invention. Suitable support platforms are well known to those skilled in the art. An example of suitable support platform is set forth, e.g., in U.S. Pat. No. 4,839,177, hereby incorporated by reference. In that patent, the support platform partially coats the tablet, and consists of a polymeric material insoluble in aqueous liquids. The support platform may, for example, be designed to maintain its impermeability characteristics during the transfer of the therapeutically active medicament. The support platform may be applied to the tablets, e.g., via compression coating onto part of the tablet surface, by spray coating the polymeric materials comprising the support platform onto all or part of the tablet surface, or by immersing the tablets in a solution of the polymeric materials.

The support platform may have a thickness of, e.g., about 2 mm if applied by compression, and about 10µ if applied via spray-coating or immersion-coating. Generally, in embodiments of the invention wherein a hydrophobic polymer or enteric coating is applied to the tablets, the tablets are coated to a weight gain from about 1 to about 20%, and in certain embodiments preferably from about 5% to about 10%.

Materials useful in the hydrophobic coatings and support platforms of the present invention include derivatives of acrylic acid (such as esters of acrylic acid, methacrylic acid, and copolymers thereof) celluloses and derivatives thereof (such as ethylcellulose), polyvinylalcohols, and the like.

In certain embodiments of the present invention, the tablet core includes an additional dose of the medicament included in either the hydrophobic or enteric coating, or in an additional overcoating coated on the outer surface of the tablet core (without the hydrophobic or enteric coating) or as a second coating layer coated on the surface of the base coating comprising the hydrophobic or enteric coating material. This may be desired when, for example, a loading dose of a therapeutically active agent is needed to provide therapeutically effective blood levels of the active agent when the formulation is first exposed to gastric fluid. The loading dose of medicament included in the coating layer may be, e.g., from about 10% to about 40% of the total amount of medicament included in the formulation.

In preferred embodiments of the invention, the final formulation provides bi-modal or multi-phasic plasma levels when the medicament is diltiazem.

In preferred embodiments, when the medicament is diltiazem, the formulations of the invention provide a first time to peak plasma concentration (Tmax #1) of the diltiazem in about 4 to about 10 hours after oral administration of the dosage form to the patient. In certain preferred embodiments, the first time to peak plasma concentration occurs from about 6 to about 8 hours after oral administration. In preferred embodiments, the maximum plasma concentration of diltiazem at the first Tmax (Cmax #1) is from about 50 to about 100 ng/ml, per administration of a 240 mg dosage of diltiazem in an oral sustained release dosage form in accordance with the invention.

In further preferred embodiments of the invention, the sustained release diltiazem formulations provide a second peak plasma concentration (Cmax #2) which occurs in about 10 to about 16 hours after oral administration of the dosage form to the patient (Tmax #2). In certain preferred embodiments, the second peak plasma concentration (Cmax #2) occurs in about 12 to about 14 hours after oral administration of the dosage form to the patient (Tmax #2). In preferred embodiments, the maximum plasma concentration of diltiazem at Cmax #2 is from about 60 to about 90 ng/ml, per 240 mg diltiazem administered over the 24 hour period.

In certain preferred embodiments, the sustained release diltiazem formulations provide a the $W_{50}$ of Cmax #1 (defined for purposes of the present invention as the width of the plasma concentration curve at 50% of the height of the first Cmax (Cmax #1), based on a trough taken at the Cmin between Cmax #1 and Cmax #2) is from about 0.5 to about 4 hours, preferably from about 1 to about 3 hours.

In certain preferred embodiments, the sustained release diltiazem formulations provide a $W_{50}$ of Cmax #2 (defined for purposes of the present invention as the width of the plasma concentration curve at 50% of the height of the second Cmax (Cmax #2), based on a the trough taken at the Cmin between Cmax #1 and Cmax #2) is from about 0.5 to about 8 hours, preferably from about 2 to about 6 hours.

In certain preferred embodiments, the sustained release diltiazem formulations of the invention provide a ratio of Cmax #1 to Cmax #2 from about 0.5:1 to about 1.5:1; preferably from about 0.7:1 to about 1.2:1.

Based on the dosage of diltiazem in the sustained release oral formulations of the invention, one can easily determine the Cmax #1, Cmax #2, Tmax #1 and Tmax #2 for different dosages of diltiazem over a 12 or 24 hour period.

In certain preferred embodiments of the invention when the medicament is oxybutynin, the formulation provides a time to peak plasma concentration (Tmax) of oxybutyrun in about 5 to about 15 hours, preferably in about 8 to about 12 hours.

Examples of soluble to highly soluble medicaments which are suitable for incorporation in the present invention include antihistamines (e.g., azatadine maleate, brompheniramine maleate, carbinoxamine maleate, chlorpheniramine maleate, dexchlorpheniramine maleate, diphenhydramine hydrochloride, doxylamine succinate, methdilazine hydrochloride, promethazine, trimeprazine tartrate, tripelennamine citrate, tripelennamine hydrochloride and triprolidine hydrochloride); antibiotics (e.g., penicillin v potassium, cloxacillin sodium, dicloxacillin sodium, nafcillin sodium, oxacillin sodium, carbenicillin indanyl sodium, oxytetracycline hydrochloride, tetracycline hydrochloride, clindamycin phosphate, clindamycin hydrochloride, clindamycin palmitate hcl, lincomycin hcl, novobiocin sodium, nitrofulrantoin sodium, metronidazole hydrochloride); antituberculosis agents (e.g., isoniazid); cholinergic agents (e.g., ambenonium chloride, bethanecol chloride, neostigmine bromide, pyridostigmine bromide); antimuscarinics (e.g., anisotropine methylbromide, clidinium bromide, dicyclomine hydrochloride, glycopyrrolate, hexocyclium methylsulfate, homatropine methylbromide, hyoscyamine sulphate, methanthehne bromide, hyoscine hydrobromide, oxyphenonium bromide, propantheline bromide, tridihexethyl chloride); sympathomimetics (e.g., bitolterol mesylate, ephedrine, ephedrine hydrochloride, ephedrine sulphate, orciprenaline sulphate, phenylpropanolamine hydrochloride, pseudoephedrine hydrochloride, ritodrine hydrochloride, salbutamol sulphate, terbutaline sulphate); sympatholytic agents (e.g., phenoxybenzamine hydrochloride); miscellaneous autonomic drugs (e.g., nicotine); iron preparations (e.g., ferrous gluconate, ferrous sulphate); haemostatics (e.g., anuinocaproic acid); cardiac drugs (e.g., acebutolol hydrochloride, disopyramide phosphate, flecainide acetate, procainamide hydrochloride, propranolol hydrochloride, quinidine gluconate, timolol maleate, tocainide hydrochloride, verapamil hydrochloride); antihypertensive agents (e.g., captopril, clonidine hydrochloride, hydralazine hydrochloride; mecamylamine hydrochloride, metoprolol tartrate); vasodilators (e.g., papaverine hydrochloride); non-steroidal anti-inflammatory agents (e.g., choline salicylate, magnesium salicylate, meclofenamate sodium, naproxen sodium, tolmetin sodium); anticonvulsants (e.g., phenobarbital sodium, phenytoin sodium, troxidone, ethosuximide, valproate sodium); tranquilizers (e.g., acetophenazine maleate, chlorpromazine hydrochloride, fluphenazine hydrochloride, prochlorperazine edisylate, promethazine hydrochloride, thioridazine hydrochloride, trifluoroperazine hydrochloride, lithium citrate, molindone hydrochloride, thiothixine hydrochloride); stimulants (e.g. benzamphetamine hydrochloride, dextroamphetamine sulphate, dextroamphetamine phosphate, diethylpropion hydrochloride, fenfluramine hydrochloride, methamphetamine hydrochloride, methylphenidate hydrochloride, phendimetrazine tartrate, phenmetrazine hydrochloride, caffeine citrate); barbiturates (e.g., amylobarbital sodium, butabarbital sodium, secobarbital sodium); sedatives (e.g., hydroxyzine hydrochloride, methprylon); expectorants (e.g., potassium iodide); antiemetics (e.g., benzaquinamide hydrochloride, metoclopropamide hydrochloride, trimethobenzamide hydrochloride); gastrointestinal drugs (e.g., ranitidine hydrochloride); heavy metal antagonists (e.g., penicillamine, penicillamine hydrochloride); antithyroid agents (e.g., methimazole); genitourinary smooth muscle relaxants (e.g., flavoxate hydrochloride); vitamins (e.g., thiamine hydrochloride, ascorbic acids); unclassified agents (e.g., amantadine hydrochloride, colchicine, etidronate disodium, leucovorin calcium, methylene blue, potassium chloride, pralidoxime chloride. This list is not meant to be exclusive.

DETAILED DESCRIPTION OF THE PREFERRED EMBODIMENTS

The following examples illustrate various aspects of the present invention They are not to be construed to limit the claims in any manner whatsoever.

Examples 1-2

Effect of Drug:Gum Ratio in Formulation

In Example 1-2, sustained release excipients in accordance with the present invention are first prepared, the medicament (in this case diltiazem) and the pH modifying agent (in this case being fumaric acid) being added subsequently, and the final mixture then being tableted.

The sustained release excipient is prepared by dry blending the requisite amounts of xanthan gum, locust bean gum, and dextrose in a high speed mixer/granulator for 3 minutes. While running choppers/impellers, water is added to the dry blended mixture, and granulated for another 3 minutes. The granulation is then dried in a fluid bed dryer to a LOD (loss on drying) of less than about 10% by weight (e.g., 4-7% LOD). The granulation is then milled using 20 mesh screens and dispensed into a granulator. The ingredients of the granulations of Examples 1-2 are set forth in Table 1 below:

TABLE 1

| | PREPARATION OF SUSTAINED-RELEASE EXCIPIENT | | |
|---|---|---|---|
| | Component | Amount (%) - Ex. 1 | Amount (%) - Ex. 2 |
| 1. | Xanthan Gum | 20 | 12 |
| 2. | Locust Bean Gum | 30 | 18 |
| 3 | Dextrose | 50 | 70 |
| 4 | Water | 30 | 25 |

Next, the desired amount of diltiazem, fumaric acid and a suitable amount of water are mixed for 5 minutes with an impeller type mixer to form a slurry. The slurry is then added to the sustained release excipient over a 1 minute-interval in the granulator, with the impeller running on low speed. Next, the mixture is granulated for 2 minutes with the chopper and impeller on high speed (additional water and granulation time may be used to form proper granules). The resultant granules are then dried in a fluid bed dryer until LOD is less than 5% and milled with hammer forward at 2000-3000 rpm. The milled granulation is then placed in a V-Blender with sodium lauryl sulfate and blended for 10 minutes. A suitable tableting lubricant (Pruv®, sodium stearyl fumarate, NF, commercially available from Penwest Pharmaceuticals Co. is added, and the mixture is blended for another 3 minutes. The resultant granulation is then compressed into tablets using a capsule shaped punch. This final mixture is tableted to approximately 768 mg. The ingredients of the tablets of Examples 1-2 are set forth in Table 2 below:

TABLE 2

TABLET FORMULATION - EXAMPLES 1-2

| | Component | Amount (%) | Amount (mg/tab) |
|---|---|---|---|
| 1. | Sustained-Release Excipient | 52.1 | 400.0 |
| 2. | Diltiazem | 31.3 | 240.0 |
| 3. | Fumaric Acid | 5.2 | 40.0 |
| 4 | Sodium Laurel Sulfate | 10.4 | 80.0 |
| 5 | Pruv ® (Sodium Stearyl Fumarate) | 1.0 | 8.0 |
| 6. | Water* | 27.5 | 0.0 |

*Removed during processing

The final tablets have a tablet weight of 768.0 mg and a hardness of 15 Kp.

Dissolution tests were then carried out on the tablets of Examples 1-2 in 900 ML water in an automated USP dissolution apparatus (Paddle type II, 100 rpm), and the amount of drug released was analyzed via UV analysis. The in-vitro dissolution results are set forth in FIG. 1 and in Table 3 below.

TABLE 3

| Time (hr) | Ex. 1 (% dissolved) | Ex. 2 (% dissolved) |
|---|---|---|
| 0 | 0.0 | 0.0 |
| 1 | 13.4 | 8.3 |
| 2 | 19.0 | 12.4 |
| 4 | 28.4 | 18.4 |
| 8 | 40.9 | 29.0 |
| 12 | 52.3 | 38.2 |
| 16 | 63.1 | 44.4 |
| 20 | 70.1 | 49.9 |
| 24 | 78.2 | 55.3 |

From the results provided in FIG. 1 and Table 3, it is evident that the rate of release of diltiazem is slower as the amount of gum in the formulations is increased.

Examples 3-4

Effect of Gum:Dextrose Ratio

In Examples 3-4, a sustained release excipient is prepared in accordance with the procedure set forth in Examples 1 and 2. The ingredients of the sustained release excipient of Examples 3 and 4 are set forth in table 4 below:

TABLE 4

| | Component | Amount (%) - Ex. 1 | Amount (%) - Ex. 2 |
|---|---|---|---|
| 1 | Xanthan Gum | 12 | 20 |
| 2 | Locust Bean Gum | 18 | 30 |
| 3 | Dextrose | 70 | 50 |
| 4 | Water* | 25 | 35 |

*removed during processing

Thereafter, diltiazem tablets are prepared as follows:

The desired amount of diltiazem, fumaric acid and the sustained release excipient are placed in a granulator and mixed for 3 minutes at low speed. Water is added over a 2 minute interval while the impeller is running at low speed (additional water and granulation time may be used to form proper granules). The resultant granules are then dried in a fluid bed dryer until LOD is less than 5% and milled with hammer forward at 2000-3000 rpm using screen #0050. The milled granulation is then placed in a V-Blender with sodium lauryl sulfate and blended for 10 minutes. A suitable tableting lubricant (Pruv®, sodium stearyl fumarate, NF, commercially available from Penwest Pharmaceuticals Co.) is added, and the mixture is blended for another 5 minutes. The resultant granulation is then compressed into tablets using a capsule shaped punch. This final mixture is tableted to approximately 750 mg. The ingredients of the tablets of Examples 3-4 are set forth in Table 5 below:

TABLE 5

TABLET FORMULATION - EXAMPLES 3-4

| | Component | Amount (%) | Amount (mg/tab) |
|---|---|---|---|
| 1. | Sustained-Release Excipient | 53.3 | 400.0 |
| 2. | Diltiazem | 32.0 | 240.0 |
| 3. | Fumaric Acid | 8.0 | 60.0 |
| 4. | Sodium Laurel Sulfate | 5.3 | 40.0 |
| 5. | Pruv ® (Sodium Stearyl Fumarate) | 1.3 | 10.0 |
| 6. | Water* | 27.5 | 0.0 |

*Removed during processing

The final tablets have a tablet weight of 750.0 mg and a hardness of 15 Kp

Dissolution tests were then carried out on the tablets of Examples 3-4 in 250 ML buffer (ph 6) in an automated USP dissolution apparatus (Paddle type III, 15 CPM), and the amount of drug released was analyzed via UV analysis. The in-vitro dissolution results are set forth in FIG. 2 and in Table 6 below:

TABLE 6

| Time (hr) | Ex. 3 (% dissolved) | Ex. 4 (% dissolved) |
|---|---|---|
| 0 | 0.0 | 0.0 |
| 1 | 20.1 | 14.3 |
| 3 | 36.5 | 25.2 |
| 8 | 64.7 | 45.5 |
| 12 | 88.3 | 57.2 |
| 16 | 102.2 | 67.4 |
| 24 | 103.6 | 86.2 |

Figure 2:
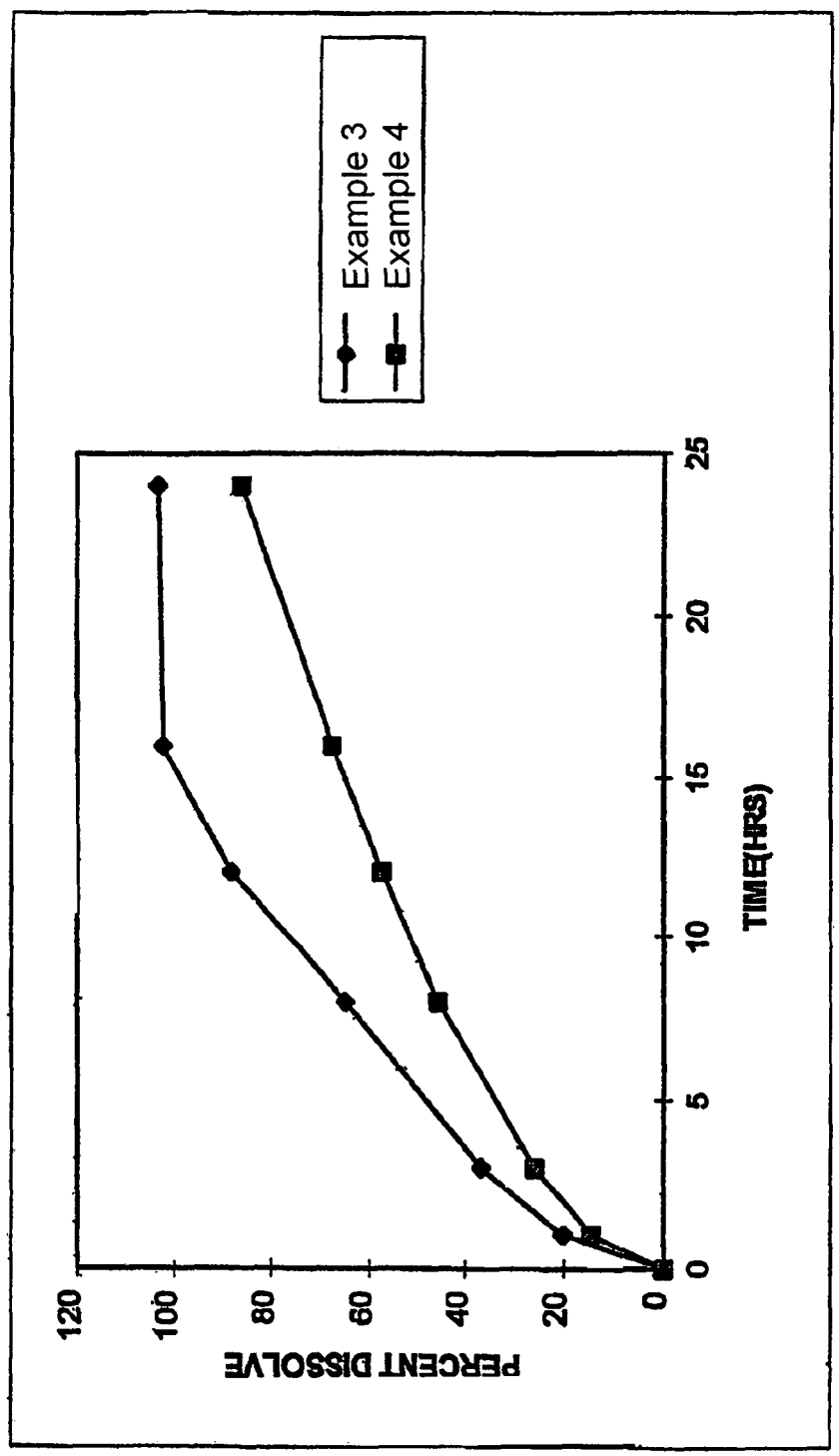
FIG. 2 is a graphical representation of the dissolution (mean percent dissolved over time) for Examples 3 and 4.

From the results provided in FIG. 2 and Table 6, it is evident that as the amount of gum relative to the amount of dextrose is increased, a corresponding decrease in drug release is observed.

Examples 5-6

Effect of Surfactant Type

In Examples 5-6, a sustained release excipient is prepared accordance with the procedure set forth in Examples 1 and 2. The ingredients of the sustained release excipient of Examples 5 and 6 are set forth in table 7 below:

TABLE 7

| | Component | Amount (%) - Ex. 5-6 |
|---|---|---|
| 1 | Xanthan Gum | 12 |
| 2 | Locust Bean Gum | 18 |
| 3 | Dextrose | 70 |
| 4 | Water* | 25 |

*removed during processing

Thereafter, diltiazem tablets are prepared as follow:

The desired amount of diltiazem, fumaric acid and a suitable amount of water are mixed for 5 minutes with an impeller type mixer to form a slurry. The slurry is then added to the sustained release excipient over a 1 minute interval in the granulator, with the impeller running on low speed. Next, the mixture is granulated for 2 minutes with the chopper and impeller on high speed (additional water and granulation time may be used to form proper granules). The resultant granules are then dried in a fluid bed dryer until LOD is less than 5% and milled with hammer forward at 2000-3000 rpm. The milled granulation of Example 5 is then placed in a V-Blender with sodium lauryl sulfate, and the milled granulation of Example 6 is placed in a V-Blender with docusate sodium and blended for 10 minutes. A suitable tableting lubricant (Pruv®, sodium stearyl fumarate, NF, commercially available from Penwest Pharmaceuticals Co. is then added to each, example, and the mixtures are blended for another 3 minutes. The resultant granulations are then compressed into tablets using a capsule shaped punch. This final mixture is tableted to approximately 848 mg. The ingredients of the tablets of Examples 5-6 are set forth in Table 8 below:

TABLE 8

TABLET FORMULATION - EXAMPLES 5-6

| | Component | Amount (%) (Ex. 5) | Amount (%) (Ex. 6) |
|---|---|---|---|
| 1. | Sustained-Release Excipient | 47.2 | 47.2 |
| 2. | Diltiazem | 28.3 | 28.3 |
| 3. | Fumaric Acid | 14.2 | 14.2 |
| 4. | Sodium Laurel Sulfate | 9.4 | N/A |
| 5 | Docusate Sodium | N/A | 9.4 |
| 6 | Pruv ® (Sodium Stearyl Fumarate) | 0.9 | 0.9 |
| 7. | Water* | 26.5 | 26.5 |

| | Component | Amount (mg/tab) (Ex. 5) | Amount (mg/tab) (Ex. 6) |
|---|---|---|---|
| 1 | Sustained-Release Excipient | 400.0 | 400.0 |
| 2 | Diltiazem | 240.0 | 240.0 |
| 3 | Fumaric Acid | 120.0 | 120.0 |
| 4 | Sodium Laurel Sulfate | 80.0 | N/A |
| 5 | Docusate Sodium | N/A | 80.0 |
| 6 | Pruv ® (Sodium Stearyl Fumarate) | 8.0 | 8.0 |

*Removed during processing

The final tablets have a tablet weight of 848.0 mg. and a hardness of 15 Kp.

Dissolution tests were then carried out on the tablets of Examples 1-2. The dissolution tests were conducted in 900 ML water in an automated USP dissolution apparatus. (Paddle type II, 100 rpm), and the amount of drug released was analyzed via UV analysis. The in-vitro dissolution results are set forth in FIG. 3 and in Table 9 below.

TABLE 9

| Time (hr) | Ex. 5 (% dissolved) | Ex. 6 (% dissolved) |
|---|---|---|
| 0 | 0.0 | 0.0 |
| 1 | 14.0 | 12.2 |
| 2 | 19.3 | 18.9 |
| 4 | 31.3 | 29.8 |
| 8 | 49.5 | 47.6 |
| 12 | 62.7 | 61.4 |
| 16 | 77.0 | 73.0 |
| 20 | 88.5 | 83.5 |
| 24 | 98.6 | 89.2 |

Figure 3:
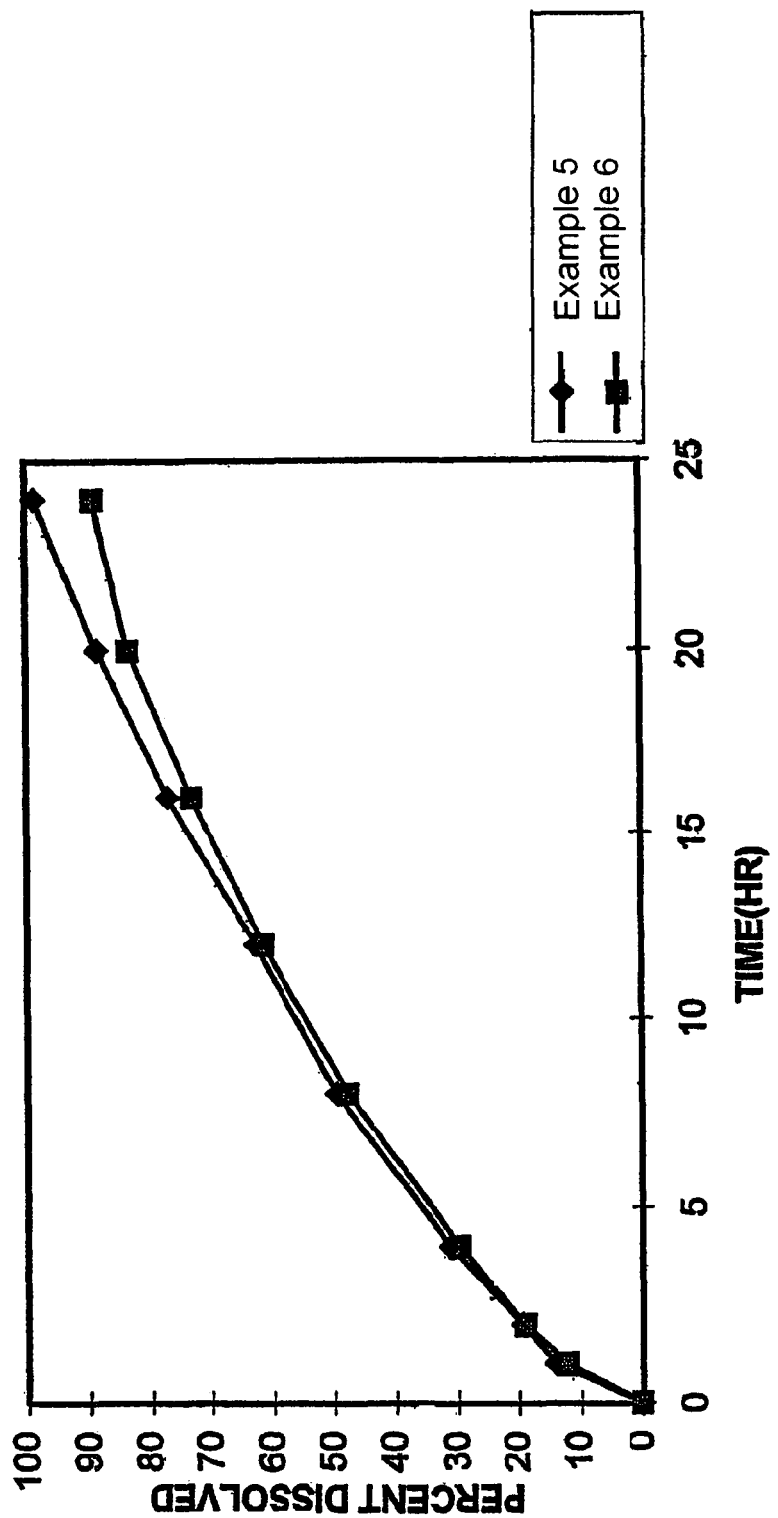
FIG. 3 is a graphical representation of the dissolution (mean percent dissolved over time) for Examples 5 and 6.

From the results provided in FIG. 3 and Table 9, it is evident that the rate of release of diltiazem is similar for equivalent ratios of sodium lauryl sulfate and docusate sodium. However, the formulation did process better with sodium lauryl sulfate.

Examples 7-8

Effect of Surfactant Level

In Examples 7-8, a sustained release excipient is prepared accordance with the procedure set forth in Examples 1 and 2. The ingredients of the sustained release excipient of Examples 7 and 8 are set forth in table 10 below:

TABLE 10

| | Component | Amount (% -) Ex. 7-8 |
|---|---|---|
| 1. | Xanthan Gum | 12 |
| 2. | Locust Bean Gum | 18 |
| 3. | Dextrose | 70 |
| 4. | Water* | 25 |

*Removed during processing

Thereafter, diltiazem tablets are prepared as follows:

The desired amount of diltiazem, fumaric acid and a suitable amount of water are mixed for 5 minutes with an impeller type mixer to form a slurry. The slurry is then added to sustained release excipient over a 1 minute interval in the granulator, with the impeller running on low speed. Next, the mixture is granulated for 2 minutes with the chopper and impeller on high speed (additional water and granulation time may be used to form proper granules). The resultant granules are then dried in a fluid bed dryer until LOD is less than 5% and milled with hammer forward at 2000-3000 rpm. The milled granulation is then placed in a V-Blender with sodium lauryl sulfate and blended for 10 minutes. A suitable tableting lubricant (Pruv®, sodium stearyl fumarate, NF, commercially available from Penwest Pharmaceuticals Co. is then added, and the mixture is blended for another 3 minutes. The resultant granulation is then compressed into tablets using a capsule shaped punch. This final mixture is tableted to approximately 768 mg. The ingredients of the tablets of Examples 7-8 are set forth in Table 11 below:

TABLE 11

TABLET FORMULATION - EXAMPLES 7-8

| | Component | Amount (%) (Ex. 7) | Amount (%) (Ex. 8) |
|---|---|---|---|
| 1. | Sustained-Release Excipient | 52.1 | 54.9 |
| 2. | Diltiazem | 31.3 | 33.0 |
| 3. | Fumaric Acid | 5.2 | 5.5 |
| 4. | Sodium Laurel Sulfate | 10.4 | 5.5 |
| 5 | Pruv ® (Sodium Stearyl Fumarate) | 1.0 | 1.1 |
| 6. | Water* | 27.5 | 27.5 |

| | Component | Amount (mg/tab) (Ex. 7) | Amount (mg/tab) (Ex. 8) |
|---|---|---|---|
| 1. | Sustained-Release Excipient | 400.0 | 400.0 |
| 2. | Diltiazem | 240.0 | 240.0 |
| 3. | Fumaric Acid | 40.0 | 40.0 |
| 4. | Sodium Laurel Sulfate | 80.0 | 40.0 |
| 5. | Pruv ® Sodium Stearyl Fumarate | 8.0 | 8.0 |

*Removed during processing

The tablets of Example 7 have a tablet weight of 768.0 mg. and a hardness of 15 Kp.

The tablets of Example 8 have a tablet weight of 728.0 mg. and a hardness of 15 Kp.

Dissolution tests were then carried out on the tablets of Examples 7-8. The dissolution test were conducted in 900 ML water in an automated USP dissolution apparatus (Paddle type II, 100 rpm), and the amount of drug released was analyzed via UV analysis. The results are set forth in FIG. 4 and Table 12 below:

TABLE 12

| Time (hr) | Ex. 7 (% Dissolved) | Ex. 8 (% Dissolved) |
|---|---|---|
| 0 | 0.0 | 0.0 |
| 1 | 13.4 | 18.5 |
| 2 | 19.0 | 28.2 |
| 4 | 28.4 | 40.1 |
| 8 | 40.9 | 56.1 |
| 12 | 52.3 | 67.6 |
| 16 | 63.1 | 77.7 |
| 20 | 70.1 | 83.8 |
| 24 | 78.2 | 90.5 |

Figure 4:
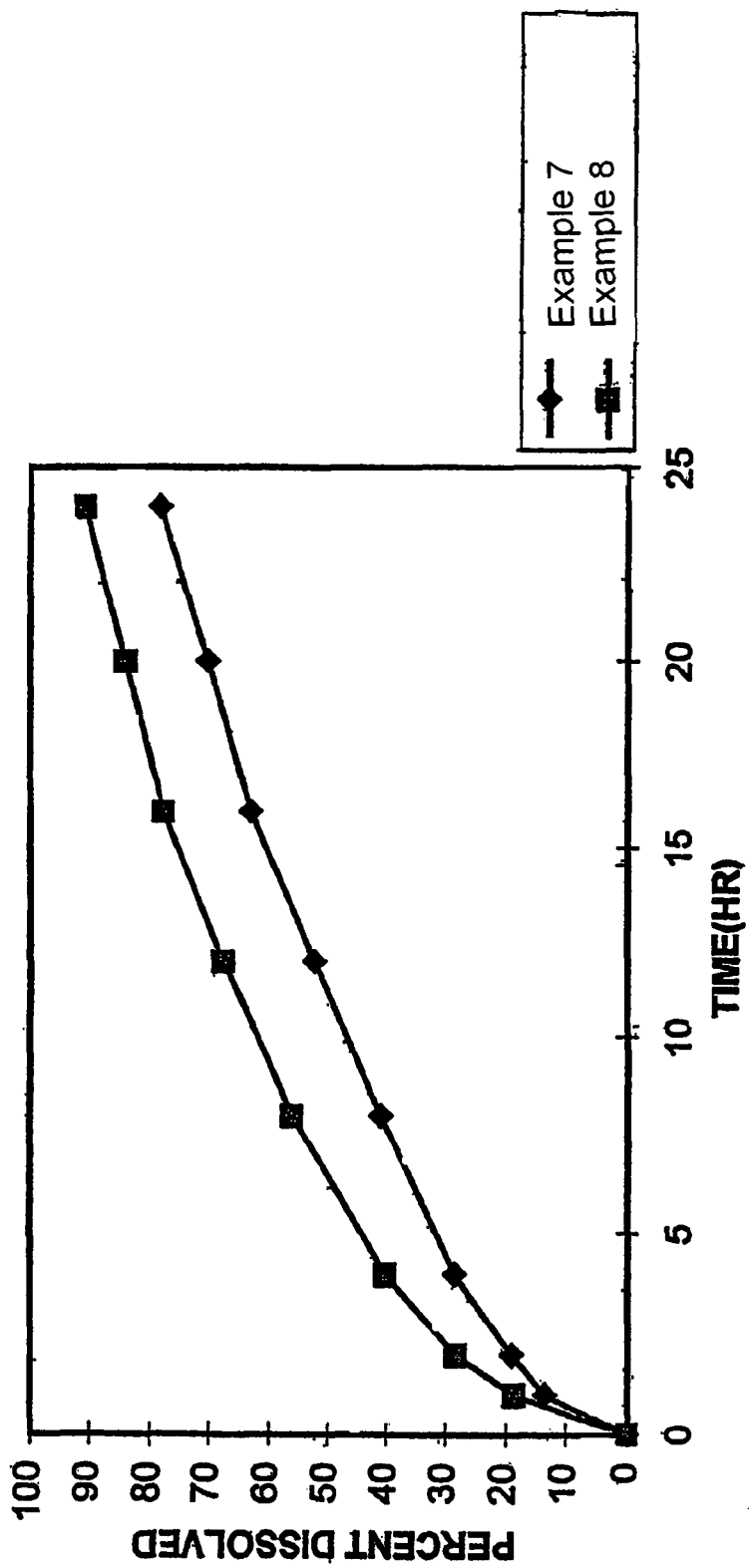
FIG. 4 is a graphical representation of the dissolution (mean percent dissolved over time) for Examples 7 and 8.

From the results provided in FIG. 4 and Table 12, it is evident that the dissolution rate of diltiazem is inversely related to the surfactant level.

Examples 9-10

Effect of Fumaric Acid Level

In Examples 9-10, a sustained release excipient is prepared accordance with the procedure set forth in Examples 1 and 2. The ingredients of the sustained release excipient of Examples 9 and 10 are set forth in table 13 below:

TABLE 13

| | Component | Amount (%) - Ex. 9-10 |
|---|---|---|
| 1. | Xanthan Gum | 12 |
| 2. | Locust Bean Gum | 18 |
| 3. | Dextrose | 70 |
| 4. | Water* | 25 |

*Removed during processing

Thereafter, diltiazem tablets are prepared as follows:

The desired amount of diltiazem, fumaric acid and a suitable amount of water are mixed for 5 minutes with an impeller, type mixer to form a slurry. The slurry is then added to sustained release excipient over a 1 minute interval in the granulator, with the impeller running on low speed. Next, the mixture is granulated for 2 minutes with the chopper and impeller on high speed (additional water and granulation time may be used to form proper granules). The resultant granules are then dried in a fluid bed dryer until LOD is less than 5% and milled with hammer forward at 2000-3000 rpm. The milled granulation is then placed in a V-Blender with sodium lauryl sulfate and blended for 10 minutes. A suitable tableting lubricant (Pruv®, sodium stearyl fumarate, NF, commercially available from Penwest Pharmaceuticals Co. is then added, and the mixture is blended for another 3 minutes. The resultant granulation is then compressed into tablets using a capsule shaped punch. This final mixture is tableted to approximately 848 mg. The ingredients of the tablets of Examples 9-10 are set forth in Table 14 below:

TABLE 14

TABLET FORMULATION - EXAMPLES 9-10

| | Component | Amount (%) (Ex. 9) | Amount (%) (Ex. 10) |
|---|---|---|---|
| 1. | Sustained-Release Excipient | 47.2 | 52.1 |
| 2. | Diltiazem | 28.3 | 31.3 |
| 3. | Fumaric Acid | 14.2 | 5.2 |
| 4. | Sodium Laurel Sulfate | 9.4 | 10.4 |
| 5. | Pruv ® (Sodium Stearyl Fumarate) | 0.9 | 1.0 |
| 6. | * Sodium Stearyl Fumarate Water* | 26.5 | 26.5 |

*Removed during processing

| | Component | Amount (mg/tab) (Ex. 9) | Amount (mg/tab) (Ex. 10) |
|---|---|---|---|
| 1. | Sustained-Release Excipient | 400.0 | 400.0 |
| 2. | Diltiazem | 240.0 | 240.0 |
| 3. | Fumaric Acid | 120.0 | 40.0 |
| 4. | Sodium Laurel Sulfate | 80.0 | 80.0 |
| 5. | Pruv ®* | 8.0 | 8.0 |

*Sodium Stearyl Fumarate

The final tablets in Example 9 have a weight of 848.0 mg. and a hardness of 15 Kp.

The final tablets in Example 10 have a weight of 768 mg. and a hardness of 15 Kp.

Dissolution tests were then carried out on the tablets of Examples 9-10. The dissolution tests were conducted in 900 ML water in an automated USP dissolution apparatus (Paddle type II, 100 rpm), and the amount of drug released was analyzed via UV analysis. The results are set forth in FIG. 5 and Table 15 below:

TABLE 15

| Time (hr) | Ex. 9 (% Dissolved) | Ex. 10 (% Dissolved) |
|---|---|---|
| 0 | 0.0 | 0.0 |
| 1 | 14.0 | 13.4 |
| 2 | 19.3 | 19.0 |
| 4 | 31.3 | 28.4 |
| 8 | 49.5 | 40.9 |
| 12 | 62.7 | 52.3 |
| 16 | 77.0 | 63.1 |
| 20 | 88.5 | 70.1 |
| 24 | 98.6 | 78.2 |

Figure 5:
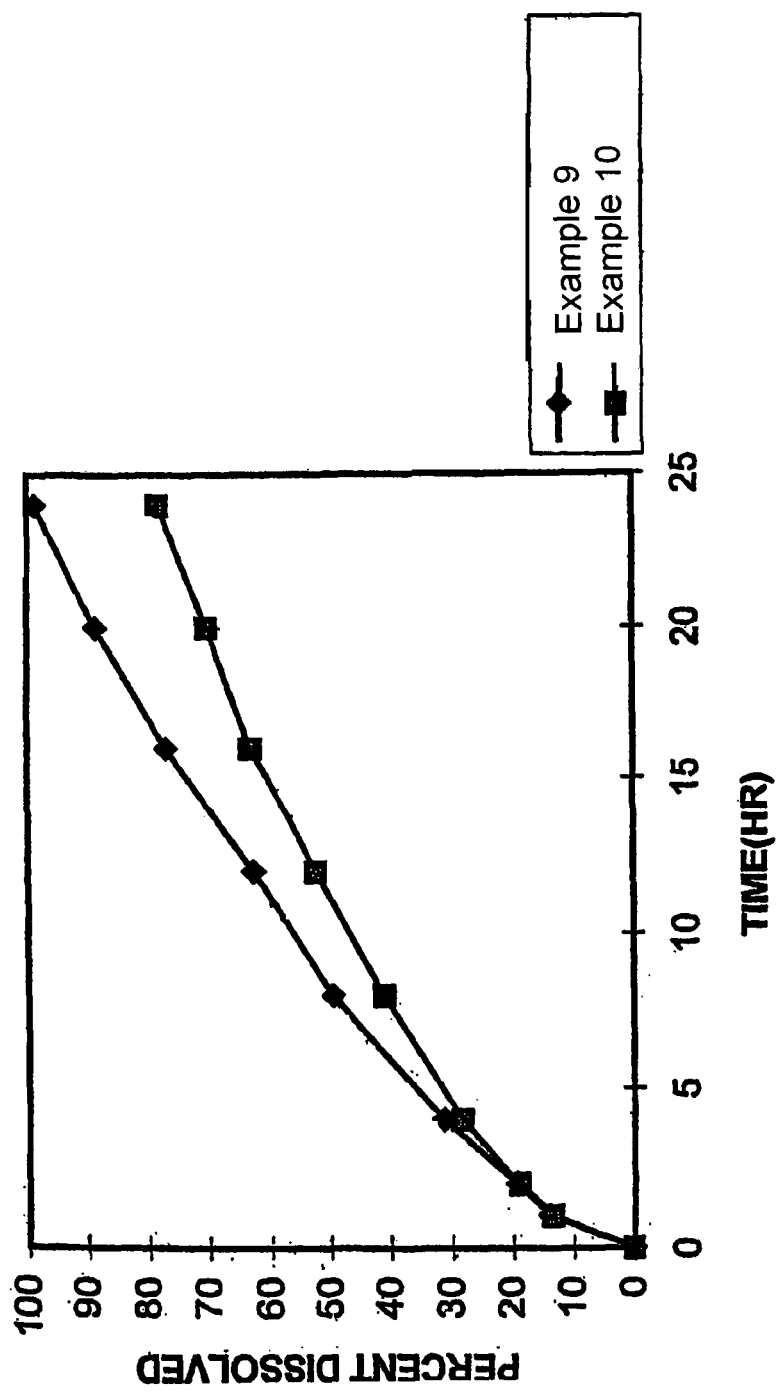
FIG. 5 is a graphical representation of the dissolution (mean percent dissolved over time) for Examples 9 and 10.

From the results provided in FIG. 5 and Table 15, it is evident that by increasing the amount of fumaric acid in the formulation, the release rate increases.

Examples 11-12

Extra-Granular Addition of Drug

In Examples 11-12, a sustained release excipient is prepared accordance with the procedure set forth in Examples 1 and 2. The ingredients of the sustained release excipient of Examples 11 and 12 are set forth in table 16 below:

TABLE 16

| | Component | Amount (%) - Ex. 11-12 |
|---|---|---|
| 1. | Xanthan Gum | 12 |
| 2. | Locust Bean Gum | 18 |
| 3. | Dextrose | 70 |
| 4. | Water* | 25 |

*Removed during processing

Thereafter, dilitiazem tablets are prepared as follows:

In Example 11, the desired amount of diltiazem, fumaric acid and a suitable amount of water are mixed for 5 minutes with an impeller type mixer to form a slurry. The slurry is then added to sustained release excipient over a 1 minute interval in the granulator, with the impeller running on low speed. Next, the mixture is granulated for 2 minutes with the chopper and impeller on high speed (additional water and granulation time may be used to form proper granules). The resultant granules are then dried in a fluid bed dryer until LOD is less than 5% and milled with hammer forward at 2000-3000 rpm. The milled granulation is then placed in a V-Blender with sodium lauryl sulfate and blended for 10 minutes. A suitable tableting lubricant (Pruv®, sodium stearyl fumarate, NF, commercially available from Penwest Pharmaceuticals Co. is then added, and the mixture is blended for another 3 minutes. The resultant granulation is then compressed into tablets using a capsule shaped punch. This final mixture is tableted to approximately 848 mg.

In Example 12, a portion of diltiazem, fumaric acid and a suitable amount of water are mixed for 5 minutes with an impeller type mixer to form a slurry. The slurry is then added to sustained release excipient over a 1 minute interval in the granulator, with the impeller running on low speed. Next, the mixture is granulated for 2 minutes with the chopper and impeller on high speed (additional water and granulation time may be used to form proper granules). The resultant granules are then dried in a fluid bed dryer until LOD is less than 5% and milled with hammer forward at 2000-3000 rpm. The milled granulation is then placed in a V-Blender with sodium lauryl sulfate and the remaining amount of diltiazem and blended for 10 minutes. A suitable tableting lubricant (Pruv®, sodium stearyl fumarate, NF, commercially available from Penwest Pharmaceuticals Co. is then added, and the mixture is blended for another 3 minutes. The resultant granulation is then compressed into tablets using a capsule shaped punch. This final mixture is tableted to approximately 848 mg. The ingredients of the tablets of Examples 11-12 are set forth in Table 17 below:

TABLE 17

TABLET FORMULATION - EXAMPLES 11-12

| Component | Amount (%) (Ex. 11) | Amount (%) (Ex. 12) |
|---|---|---|
| 1. Sustained-Release Excipient | 47.2 | 47.2 |
| 2. Diltiazem (granular) | 28.3 | 18.4 |
| 3. Diltiazem (extragranular) | N/A | 9.9 |
| 4. Fumaric Acid | 14.2 | 14.2 |
| 5. Sodium Laurel Sulfate | 9.4 | 9.4 |
| 6. Pruv ® (Sodium Stearyl Fumarate) | 0.9 | 0.9 |
| 7. Water* | 26.5 | 25.0 |

| Component | Amount (mg/tab) (Ex. 11) | Amount (mg/tab) (Ex. 12) |
|---|---|---|
| 1. Sustained-Release Excipient | 400.0 | 400.0 |
| 2. Diltiazem (granular) | 240.0 | 156.0 |
| 3. Diltiazem (extragranular) | N/A | 84.0 |
| 4. Fumaric Acid | 120.0 | 120.0 |
| 5. Sodium Laurel Sulfate | 80.0 | 80.0 |
| 6. Pruv ® (Sodium Stearyl Fumarate) | 8.0 | 8.0 |

*Removed during processing

The final tablets of Example 11 have a weight of 848.0 mg. and a hardness of 15 Kp.

The final tablets of Example 12 have a weight of 848.0 mg. and a hardness of 15 Kp.

Dissolution tests were then carried out on the tablets of Examples 11-12. The dissolution tests were conducted in 900 ML water in an automated USP dissolution apparatus (Paddle type II, 100 rpm), and the amount of drug released was analyzed via UV analysis. The results are set forth in FIG. 6 and Table 18 below:

TABLE 18

| Time (hr) | Ex. 11 (% Dissolved) | Ex. 12 (% Dissolved) |
|---|---|---|
| 0 | 0.0 | 0.0 |
| 1 | 14.2 | 32.6 |
| 2 | 19.3 | 35.5 |
| 4 | 31.3 | 48.7 |
| 8 | 49.5 | 66.4 |
| 12 | 62.7 | 78.5 |
| 16 | 77.0 | 85.2 |
| 20 | 88.5 | 89.2 |
| 24 | 98.6 | 94.6 |

Figure 6:
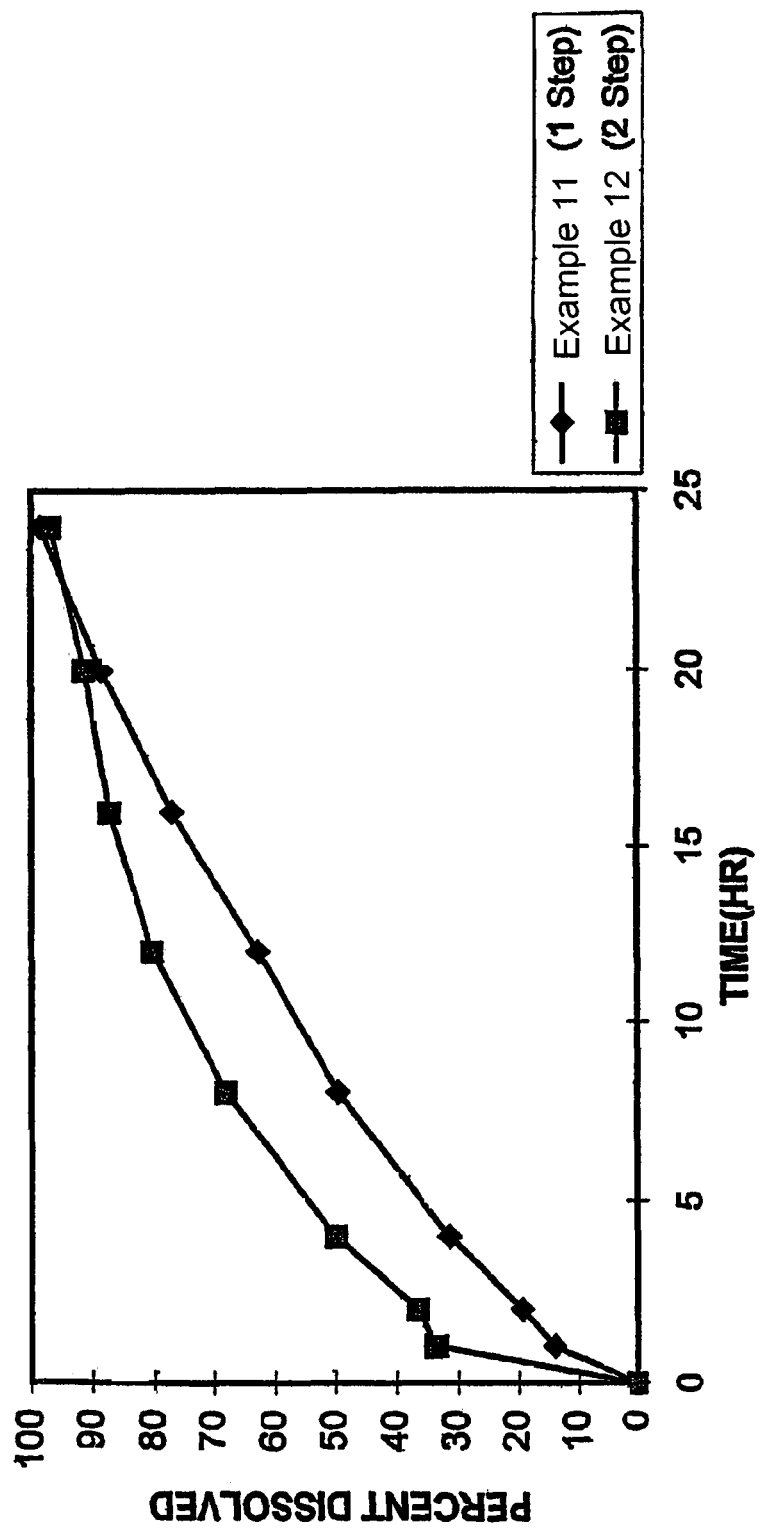
FIG. 6 is a graphical representation of the dissolution (mean percent dissolved over time) for Examples 11 and 12.
Figure 7:
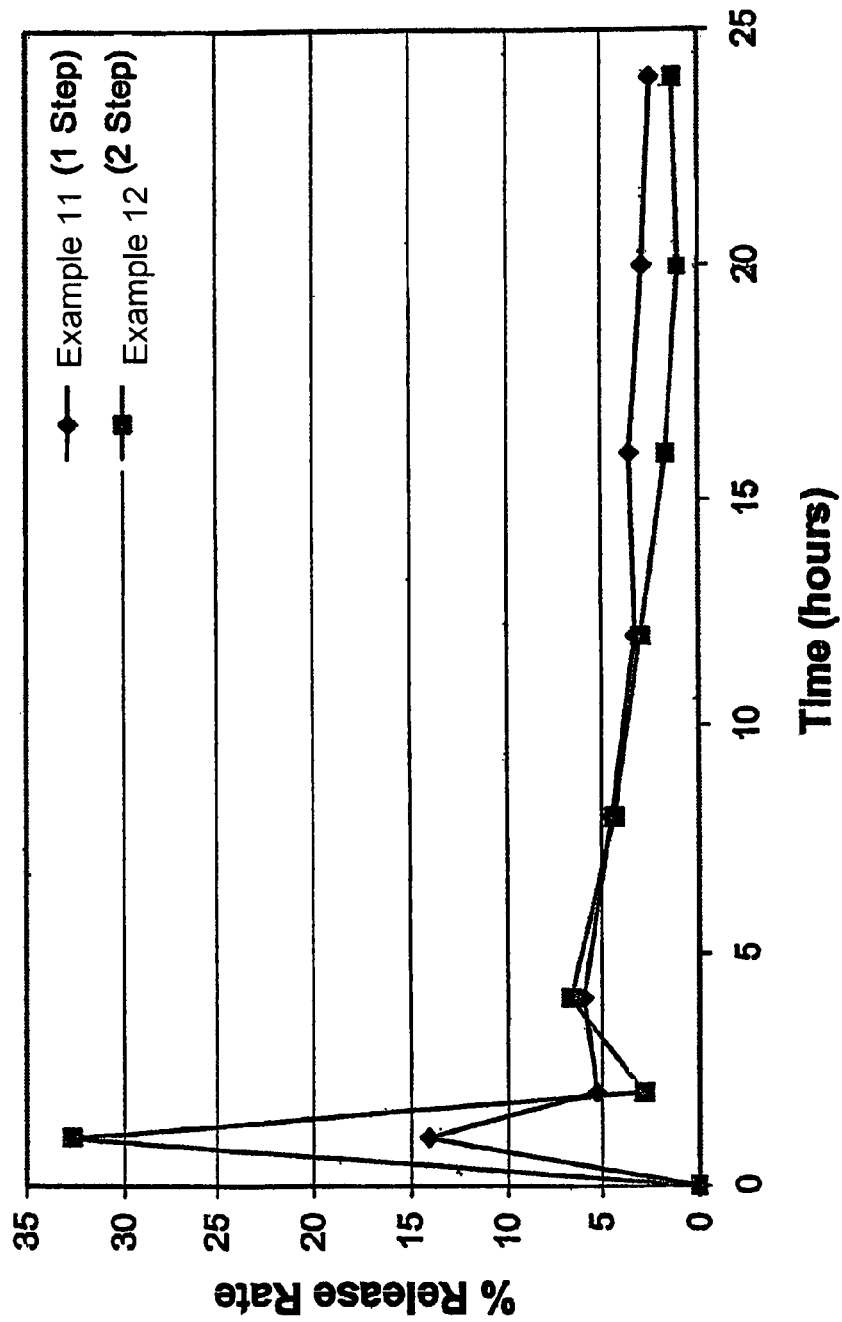
FIG. 7 is a graphical representation of the % release rate over time for Examples 11 and 12.

From the results provided in FIG. 6 and Table 18, it is shown that the addition of diltiazem extragranularly produces an initial burst of approximately 35%. It is evident that the addition of a percentage of the drug extra-granularly provides an initial rapid release, as also demonstrated by FIG. 7 which depicts the % release rate of diltiazem from the dosage forms of Examples 11 and 12 over time.

Examples 13-18

Effect of Coating Tablets with Eudragit L30D55 w/NaOH (Methacrylic Acid Copolymer Aqueous Dispersion)

In Examples 13-18, a sustained release excipient is prepared accordance with the procedure set forth in Examples 1 and 2. The ingredients of the sustained release excipient of Examples 13-18 are set forth in table 19 below:

TABLE 19

| | Component | Amount (%) - Ex. 13-18 |
|---|---|---|
| 1. | Xanthan Gum | 12 |
| 2. | Locust Bean Gum | 18 |
| 3. | Dextrose | 70 |
| 4. | Water* | 25 |

*Removed during processing

Thereafter, diltiazem tablets are prepared as follows:

The desired amount of diltiazem, fumaric acid and the sustained release excipient are mixed in a granulator for 3 minutes at low speed. A suitable amount of water is then added over a 2 minute interval with the impeller running at low speed. The resultant slurry is then granulated for 7.5 minutes with the chopper and impeller on high speed (additional water and granulation time may be used to form proper granules). The resultant granules are then dried in a fluid bed dryer until LOD is less than 5% and milled with hammer forward at 2000-3000 rpm using screen #0050. The milled granulation is then placed in a V-Blender with sodium lauryl sulfate and blended for 10 minutes. A suitable tableting lubricant (Pruv®, sodium stearyl fumarate, NF, commercially available from Penwest Pharmaceuticals Co. is then added, and the mixture is blended for another 5 minutes. The resultant granulation is then compressed into tablets using a capsule shaped punch. This final mixture is tableted to approximately 750 mg.

The ingredients of the tablets of Examples 13-18 are set forth in Table 20 below:

TABLE 20

TABLET FORMULATION - EXAMPLES 13-18

| | Component | Amount (%) |
|---|---|---|
| 1. | Sustained-Release Excipient | 53.3 |
| 2. | Diltiazem (granular) | 32.0 |
| 3. | Fumaric Acid | 8.0 |
| 4. | Sodium Laurel Sulfate | 5.3 |
| 5 | Pruv ® (Sodium Stearyl Fumarate) | 1.3 |
| 6. | Water* | 27.0 |

| | Component | Amount (mg/tab) |
|---|---|---|
| 1. | Sustained-Release Excipient | 400.0 |
| 2. | Diltiazem (granular) | 240.0 |
| 3. | Fumaric Acid | 60.0 |
| 4. | Sodium Laurel Sulfate | 40.0 |
| 5. | Pruv ® (Sodium Stearyl Fumarate) | 10.0 |

*Removed during processing

The final tablets have a tablet weight of 750.0 mg. and a hardness of 15 Kp.

The core tablets were then coated with an aqueous dispersion of Eudragit L30D55 w/NaOH, e.g., to a weight gain of 3%, 5%, 7%, and 9% (Examples 15-18, respectively) based on the weight of the whole tablet.

The aqueous dispersion was prepared by the following procedure:

1.0N sodium hydroxide solution is prepared by adding 4.0 g of sodium hydroxide to 50 ml purified water in a volumetric flask and stirring for 5-15 minutes. Purified water is then added to the necessary volume and mixed again.

The talc suspension is prepared by slowly adding 9.31 g triethyl citrate to 202.54 g purified water while stirring. While continuing to stir, 22.2 g talc is added to the container over a 3 minute interval. The container is stirred until a suspension is formed.

Eudragit suspension is then prepared by passing the Eudragit through a #40 mesh sieve and weighing out 294.52 g. Using a dropper, 1.78 g of 1.0N sodium hydroxide solution is added to the Eudragit while stirring. The mixture is stirred for 30-60 minutes.

While stirring the Eudragit suspension, the talc suspension is added over a 5 minute period and stirred for 30-60 minutes.

Dissolution tests were carried out on the tablets of Examples 13-18. The dissolution tests were conducted in 250 ML buffer (ph 6) in an automated USP dissolution apparatus (Paddle type III, 15 CPM), and the amount of drug released was analyzed via UV analysis. The results are set forth in FIG. 8 and Table 21 below:

TABLE 21

| Time (hr) | Ex. 13 Lot A (no coating) | Ex. 14 Lot B (no coating) | Ex. 15 Lot A (3% coating) |
|---|---|---|---|
| 0 | 0.0 | 0.0 | 0.0 |
| 1 | 18.4 | 18.0 | 5.4 |
| 3 | 32.6 | 32.8 | 16.0 |
| 8 | 59.8 | 60.2 | 48.9 |
| 12 | 80.5 | 77.9 | 68.2 |
| 16 | 92.3 | 93.9 | 89.6 |
| 24 | 93.7 | 98.4 | 99.0 |

| Time (hr) | Ex. 16 Lot B (coating 5%) | Ex. 17 Lot B (coating 7%) | Ex. 18 Lot B (coating 9%) |
|---|---|---|---|
| 0 | 0.0 | 0.0 | 0.0 |
| 1 | 1.9 | 0.4 | 0.4 |
| 3 | 13.8 | 11.1 | 8.9 |
| 8 | 44.1 | 36.3 | 27.5 |
| 12 | 63.4 | 54.4 | 41.8 |
| 16 | 82.4 | 77.7 | 56.8 |
| 24 | 98.3 | 99.6 | 84.6 |

Figure 8:
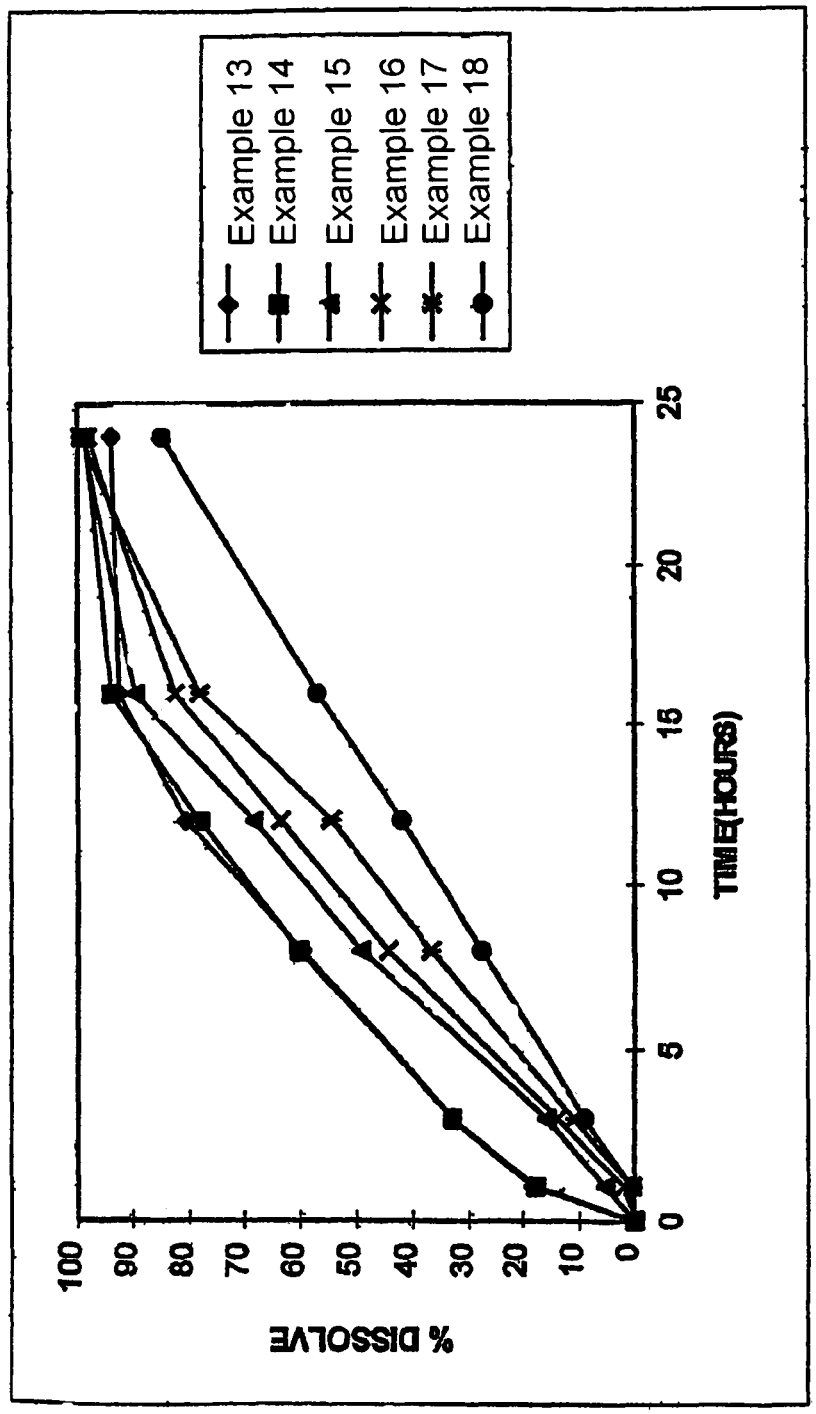
FIG. 8 is a graphical representation of the dissolution (mean percent dissolved over time) for Examples 13 and 18.

From the results provided in FIG. 8 and Table 21, it is evident that as the amount (by weight) of the coating increases, the release rate decreases.

Examples 19-20

Effect of Coating Tablets with Eudragit RS30D/RL30D(50/50) (Ammonio-Methacrylic Acid Copolymer Aqueous Dispersion)

In Examples 19-20, a sustained release excipient is prepared accordance with the procedure set forth in Examples 1 and 2. The ingredients of the sustained release excipient of Examples 19 and 20 are set forth in table 22 below:

TABLE 22

| | Component | Amount (%) - Ex. 19-20 |
|---|---|---|
| 1. | Xanthan Gum | 12 |
| 2. | Locust Bean Gum | 18 |
| 3. | Dextrose | 70 |
| 4. | Water* | 25 |

*removed during processing

Thereafter, diltiazem tablets are prepared as follows:

The desired amount of diltiazem, fumaric acid and the sustained release excipient are mixed in a granulator for 3 minutes at low speed. A suitable amount of water is then added over a 2 minute interval with the impeller running at low speed. The resultant slurry is then granulated for 6 minutes with the chopper and impeller on high speed (additional water and granulation time may be used to form proper granules). The resultant granules are then dried in a fluid bed dryer until LOD is less than 5% and milled with hammer-forward at 2000-3000 rpm using screen #0050. The milled granulation is then placed in a V-Blender with sodium lauryl sulfate and blended for 10 minutes. A suitable tableting lubricant (Pruv®, sodium stearyl fumarate, NF, commercially available from Penwest Pharmaceuticals Co. is then added, and the mixture is blended for another 3 minutes. The resultant granulation is then compressed into tablets using a capsule shaped punch. This final mixture is tableted to approximately 50 mg. The ingredients of the tablets of Examples 19-20 are set forth in FIG. 9 and Table 23 below:

TABLE 23

TABLET FORMULATION - EXAMPLES 19-20

| | Component | Amount (%) | Amount (mg/tb) |
|---|---|---|---|
| 1. | Sustained-Release Excipient | 53.3 | 400.0 |
| 2. | Diltiazem (granular) | 32.0 | 240.0 |
| 3. | Fumaric Acid | 8.0 | 60.0 |
| 4. | Sodium Laurel Sulfate | 5.3 | 40.0 |
| 5. | Pruv ® (Sodium Stearyl Fumarate) | 1.3 | 10.0 |
| 6. | Water* | 27.0 | 0.0 |

*Removed during processing

The final tablets have a weight of 750.0 mg. and a hardness of Kp 15.

The core tablet was then coated with an aqueous dispersion of Eudragit RS30D/RL30D(50/50) to a weight gain of 8%, based on the weight of the whole tablet.

The aqueous dispersion was prepared by the following procedure:

The Eudragit RS/RL suspension is prepared by mixing 100 g of Eudragit RS with 100 g of Eudragit RL.

Talc suspension is prepared by slowly adding 12.0 g triethyl citrate to 338.0 g purified water while stirring. While continuing to stir, 50.0 g talc is added to the container over a 3 minute interval. The container is stirred until a suspension is formed.

While stirring the Eudragit suspension, the talc suspension is then added over a 5 minute period. The resultant mixture is stirred for 30-60 minutes and screened through a 40 mesh sieve.

Dissolution tests were carried out on the tablets of Examples 19-20. The dissolution tests were conducted in 900 ML of 0.1N HCL in an automated USP dissolution apparatus (Paddle type II, 100 rpm), and the amount of drug released was analyzed via UV analysis. The results are set forth in FIG. 9 and Table 24 below:

TABLE 24

| Time (hr) | Ex. 19 (8% coating) | Ex. 20 (No coating) |
|---|---|---|
| 0 | 0.0 | 0.0 |
| 1 | 21.5 | 0.5 |
| 3 | 41.3 | 11.6 |
| 5 | 55.9 | 24.4 |
| 8 | 74.3 | 46.4 |
| 10 | 84.8 | 57.5 |
| 12 | 91.9 | 64.9 |
| 14 | 95.1 | 72.2 |
| 16 | 96.2 | 77.6 |
| 20 | 96.0 | 87.5 |
| 24 | 96.1 | 91.3 |

Figure 9:
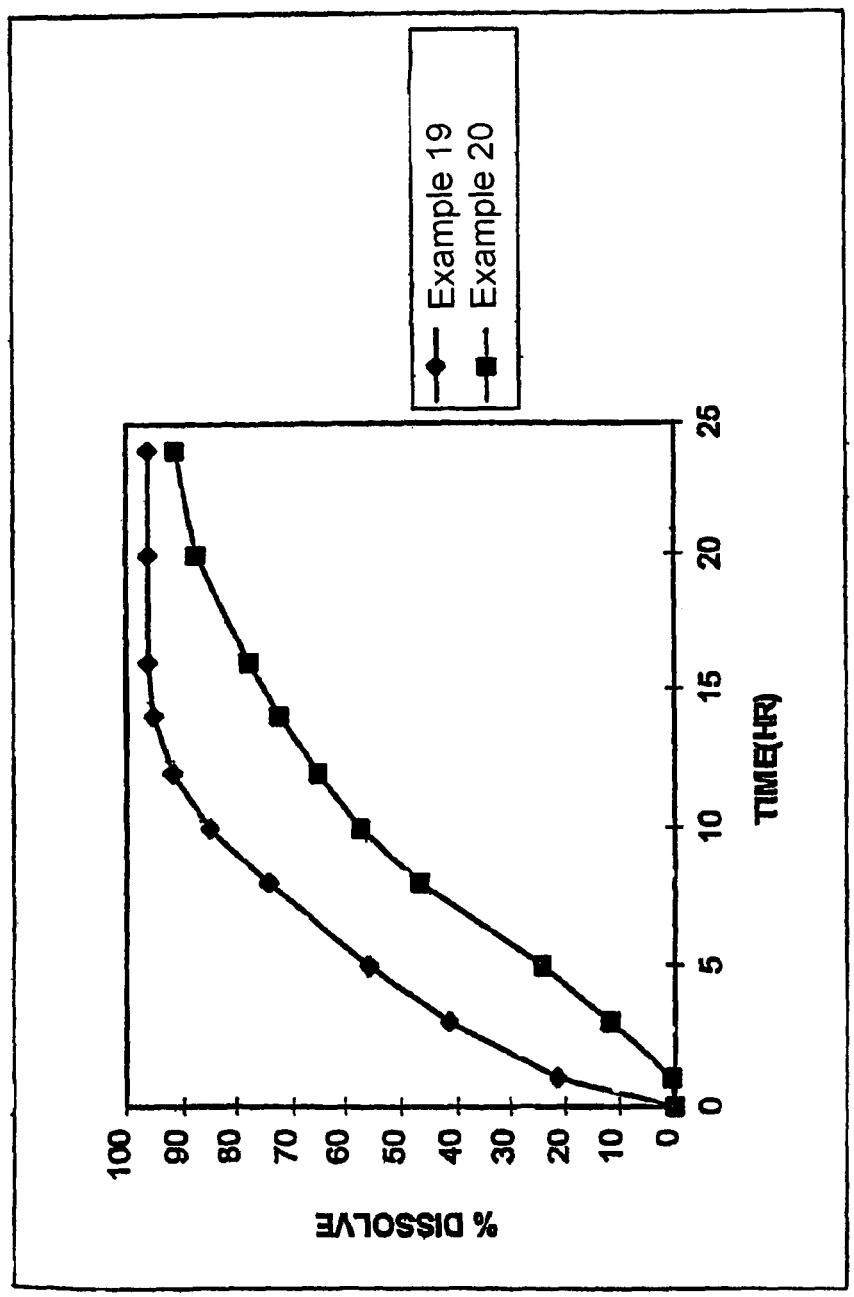
FIG. 9 is a graphical representation of the dissolution (mean percent dissolved over time) for Examples 19 and 20.

From the results provided in FIG. 9 and Table 24, it is evident that the coating-decreased the release rate.

Examples 21-23

Effect of Coating Tablets with Ethylcellulose

In Examples 21-23, a sustained release excipient is prepared accordance with the procedure set forth in Examples 1 and 2. The ingredients of the sustained release excipient of Examples 21-23 are set forth in table 25 below:

TABLE 25

| | Component | Amount (%) - Ex. 21-23 |
|---|---|---|
| 1. | Xanthan Gum | 12 |
| 2. | Locust Bean Gum | 18 |
| 3. | Dextrose | 70 |
| 4. | Water* | 25 |

*Removed during processing

Thereafter, diltiazem tablets are prepared as follows:

The desired amount of diltiazem, fumaric acid and the sustained release excipient are mixed in a granulator for 3 minutes at low speed. A suitable amount of water is then added over a 2 minute interval with the impeller running at low speed. The resultant slurry is then granulated for 3 minutes with the chopper and impaler on high speed (additional water and granulation time may be used to form proper granules). The resultant granules are then dried in a fluid bed dryer until LOD is less than 5% and milled with hammer forward at 2000-3000 rpm using screen #0050. The milled granulation is then placed in a V-Blender with sodium lauryl sulfate and blended for 10 minutes. A suitable tableting lubricant (Pruv®, sodium stearyl Fumarate, NF, commercially available from Penwest Pharmaceuticals Co. is then added, and the mixture is blended for another 3 minutes. The resultant granulation is then compressed into tablets using a capsule shaped punch. This final mixture is tableted to approximately 750 mg.

The ingredients of the tablets of Examples 21-23 are set forth in Table 26 below:

TABLE 26

TABLET FORMULATION - EXAMPLES 21-23

| | Component | Amount (%) | Amount (mg/tab) |
|---|---|---|---|
| 1. | Sustained-Release Excipient | 53.3 | 400.0 |
| 2. | Diltiazem (granular) | 32.0 | 240.0 |
| 3. | Fumaric Acid | 8.0 | 60.0 |
| 4. | Sodium Laurel Sulfate | 5.3 | 40.0 |
| 5. | Pruv ® (Sodium Stearyl Fumarate) | 1.3 | 10.0 |
| 6. | Water* | 29.0 | 0.0 |

The final tablets have a tablet weight of 750.0 mg. and a hardness of 15 Kp.

The core tablet was then coated with an aqueous dispersion of Ethylcellulose/Opadry(80/20) to a weight gain of 4% and 6% (Examples 22 and 23, respectively) based on the whole weight of the tablet. The aqueous dispersion was prepared by the following procedure:

First, 60 g of Opadry is mixed with 340 g of water in a suitable container. While continuing to mix, 944 g Ethylcellulose is added to the Opadry dispersion. The resultant mixture is stirred for 30-60 minutes.

Dissolution tests were then carried out on the tablets of Examples 1-2. The dissolution tests are conducted in 250 ML of buffer (ph 6) in an automated USP dissolution apparatus (Paddle type III, 15 CPM), and the amount of drug released was analyzed via UV analysis. The results are set forth in FIG. 10 and Table 27 below:

TABLE 27

| Time (hr) | Ex. 21 (No Coating) | Ex. 22 (4% Coating) | | Ex. 23 (6% Coating) |
|---|---|---|---|---|
| 0 | 0.0 | 0.0 | | 0.0 |
| 1 | 8.8 | 4.1 | | 0.5 |
| 3 | 39.1 | 29.8 | 1 | 2.6 |
| 8 | 69.0 | 61.2 | | 58.2 |
| 12 | 85.1 | 86.7 | | 95.5 |
| 16 | 106.6 | 99.8 | | 101.3 |
| 24 | 107.0 | 101.9 | | 101.5 |

Figure 10:
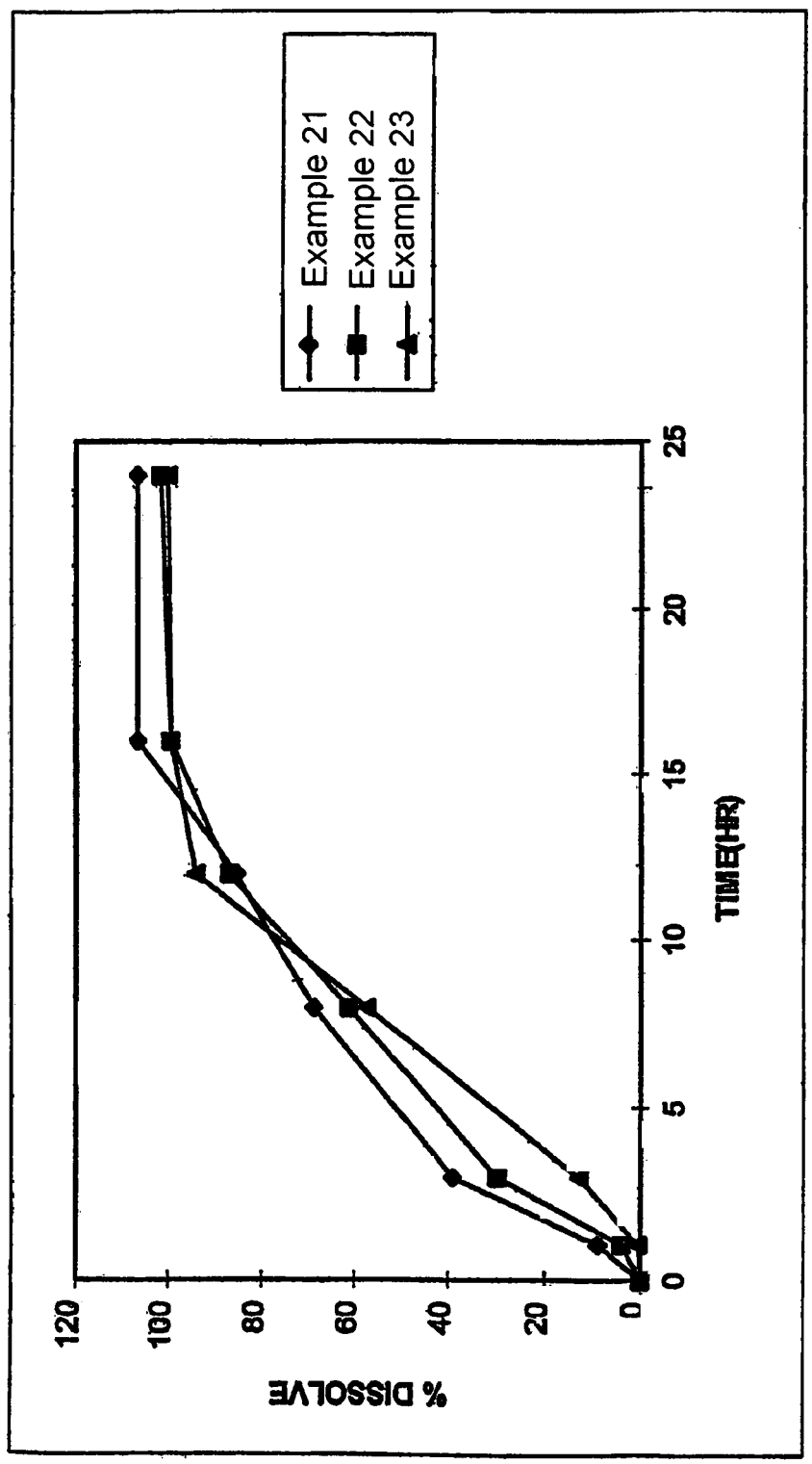
FIG. 10 is a graphical representation of the dissolution (mean percent dissolved over time) for Examples 21-23.

From the results provided in FIG. 10 and Table 27, it is evident that as the amount of coating increased, the release rate decreased.

Examples 24-25

Effect of Excipient Addition Outside Granulation

In Examples 24-25, a sustained release excipient is prepared in accordance with the procedure in Examples 1 and 2. The ingredients of the sustained release excipient of Examples 24 and 25 are set forth in Table 28 below:

TABLE 28

| Component | Amount (%) Ex. 25 | Amount (%) Ex. 26 |
|---|---|---|
| 1. xanthan Gum | 12 | 12 |
| 2. Locust Bean Gum | 18 | 18 |
| 3. Dextrose | 70 | 70 |
| 4. Water* | 25 | 25 |

*Removed during processing.

Next, tablets were manufactured in accordance with the ingredients of Table 29 and the procedure that follows:

TABLE 29

| Component | (%) Ex. 24 | mg/tab Ex. 24 | (%) Ex. 25 | mg/tab Ex 25 |
|---|---|---|---|---|
| 1. Sustained Release Excipient | 49.2 | 400.0 | 53.3 | 400.0 |
| 2. Diltiazem HCL (Intragranular) | 19.2 | 156.0 | 32.0 | 240.0 |
| 3. Diltiazem HCI (Extra granular) | 10.3 | 84.0 | N/A | N/A |
| 4. Fumaric Acid | 14.8 | 120.0 | 8.0 | 60.0 |
| 5. Surfactant (SLS) | 4.9 | 40.0 | 5.3 | 40.0 |
| 6. Sodium Stearyl Fumarate, NF | 1.6 | 13.0 | 1.3 | 10.0 |
| 7. Water* | 27.0 | 0.0 | 27.0 | 0.0 |

*Removed during processing

The final tablets of Example 24 have a tablet weight of 813.0 mg. and a hardness of 15 Kp.

The final tablets of Example 25 have a tablet weight of 750.0 mg. and a hardness of 15 Kp.

The procedure for preparing the formulations of Examples 24-25 is as follows:

The desired amount of (1), (2), and (4) are dispensed into a granulator and mixed for 3 minutes at low speed; while running the impeller at low speed, (7) is added over a 2 minute interval; the mixture is granulated for 7.5 minutes with the chopper and the impeller on high speed (additional water and granulation time may be used to form proper granules); the granulated mixture is dried in a fluid bed dryer until the LOD is less than 5%; the dried granulation is milled with the hammer forward at 2000-3000 rpm using screen #0050; the milled granulation and (5) or (3&5) are placed in a V-Blender and blended for 10 minutes; (6) is added to the V-Blender and blended for 5 minutes. The final mixture is compressed into tablets using a capsule shaped punch.

The Eudragit® L30D55 w/NaOH Coating Dispersion was prepared as follows:

A. 1.0N Sodium Hydroxide solution was prepared by adding 4.0 g of Sodium Hydroxide to a 100 ml volumetric flask; then 50 ml of Purified water and a magnetic stir bar were added into the flask and the contents of the flask were mixed for 5-15 minutes; the stir bar was removed and the volume was Q.S. and mixed.

B. Talc suspension was prepared by weighing 202.54 g of Purified water in a suitable container; 9.31 g of Triethyl Citrate was slowly added while the Purified water was stirred; then 22.22 g of Talc was added over a 2 minute interval to the container while the mixture was stirred (the mixture was stirred until a suspension formed).

C. Eudragit® L30D55 Suspension was prepared by passing the Eudragit® L30D55 through a #40 mesh sieve; 294.52 g of sieved Eudragite L30D55 was weighed and placed into a suitable container; using a dropper, 3.56 g of the 1.0N Sodium Hydroxide solution (StepA) was added while the mixture was stirred; the mixture was stirred for 30-60 minutes.

D. The final Coating Suspension was prepared by stirring the Eudragite L30D55 Suspension (Step C) while Talc suspension (step B) was added over a 5 minute period; the mixture was stirred for 30-60 minutes.

The tablets were coated for a weight gain of 4% based on the whole weight of the tablet. The tablets were encapsulated by placing the coated tablets into clear gelatin capsules.

Plasma-Profile of Example 24

In-vivo studies were performed with the tablet of Example 24 using a two way randomized, open label crossover design in healthy volunteers, 12 subjects for each, and they were dosed in the fasted state and compared with CARDIZEM CD®. The results are set forth in FIG. 11 and in Tablet 30 below:

TABLE 30

| Time (hours) | Ex. 24 Fasted (ng/ml) | Cardizem-CD Fasted (ng/ml) |
|---|---|---|
| 0 | 0.00 | 0.00 |
| 1 | 0.65 | 0.00 |
| 2 | 4.72 | 0.00 |
| 4 | 31.02 | 19.65 |
| 6 | 62.45 | 83.08 |
| 7 | 63.27 | 60.98 |
| 8 | 65.45 | 50.79 |
| 9 | 64.20 | 42.52 |
| 10 | 65.39 | 38.43 |
| 12 | 77.30 | 42.56 |
| 14 | 82.86 | 52.58 |
| 15 | 81.91 | 56.40 |
| 16 | 80.17 | 57.48 |
| 18 | 70.09 | 57.73 |
| 20 | 57.59 | 51.97 |
| 24 | 42.21 | 43.48 |
| 30 | 24.82 | 28.73 |
| 36 | 10.97 | 12.8 |
| 48 | 2.55 | 3.78 |

Ratio

The ratio of the area are under the curve between Example 24 and CARDIZEM CD® 240 mg was 1.16:1. The ratio of the average, Cmax between Example 25 and Cardizem CD 240 was 1.16:1.

Outcome

Figure 11:
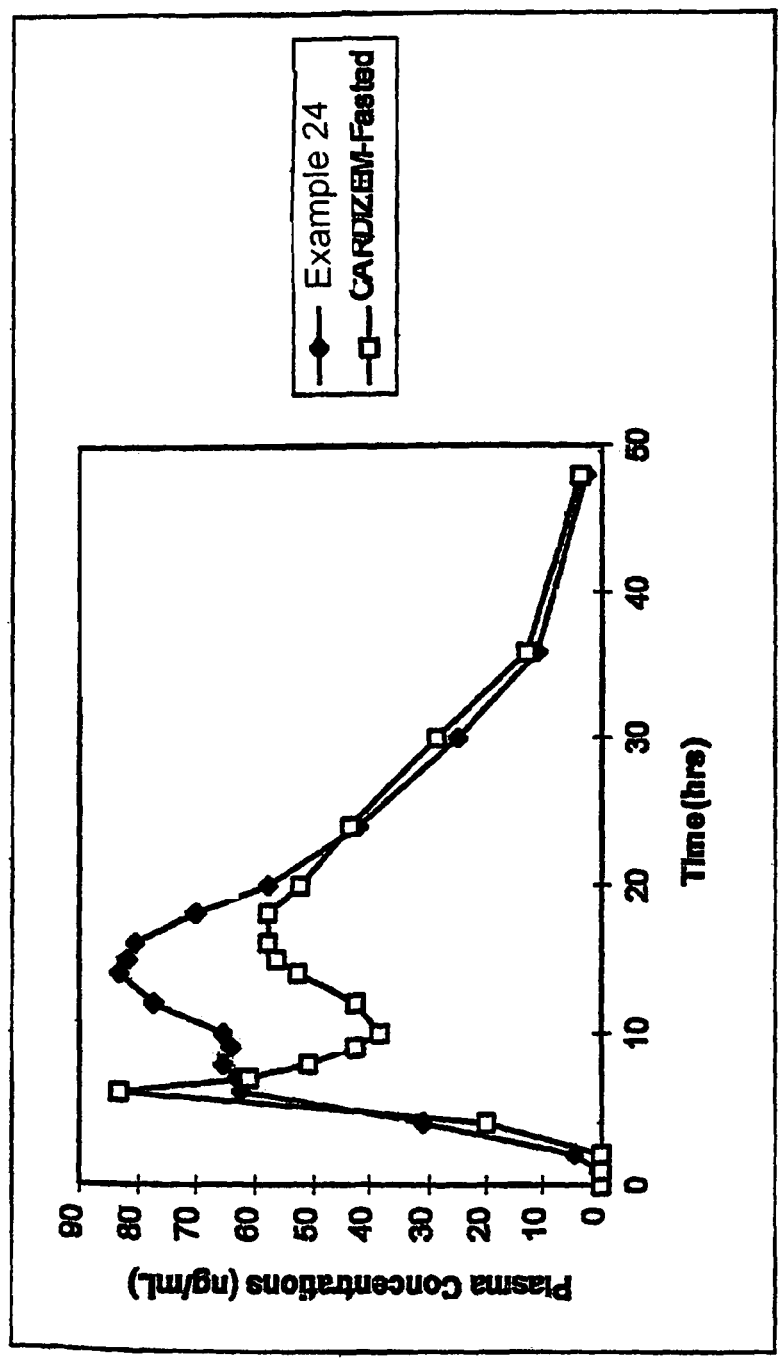
FIG. 11 is a graphical representation of the mean plasma diltiazem concentration (ng/ml) over time for Example 24 and for a reference standard (Cardizem CD 240 mg).

FIG. 11 and Example 24 demonstrated a Bi-Modal plasma level in-vivo, the CARDIZEM CD® also demonstrated Bi-Modal plasma levels by the mixture of two differently processed bead formulations.

Plasma Profile of Example 25

In-vivo studies were performed with the tablets of Example 25 using a two way randomized, open label crossover design in healthy volunteers, 12 subjects for each and they were dosed in the fasted state and compared with CARDIZEM CD®. The results set forth in FIG. 12 in Table 31 below:

TABLE 31

| Time (hours) | EXAMPLE Fasted (ng\ml) | Cardizem-CD Fasted (ng\ml) |
|---|---|---|
| 0 | 0.00 | 0.00 |
| 1 | 0.30 | 0.05 |
| 2 | 6.55 | 0.40 |
| 4 | 35.43 | 5.48 |
| 6 | 77.71 | 66.02 |
| 7 | 76.91 | 58.31 |

TABLE 31-continued

| Time (hours) | EXAMPLE Fasted (ng\ml) | Cardizem-CD Fasted (ng\ml) |
|---|---|---|
| 8 | 70.88 | 47.29 |
| 9 | 66.18 | 39.31 |
| 10 | 64.98 | 35.51 |
| 12 | 71.90 | 38.55 |
| 14 | 65.48 | 41.66 |
| 15 | 62.72 | 47.32 |
| 16 | 60.60 | 49.73 |
| 18 | 48.87 | 51.16 |
| 20 | 38.95 | 45.75 |
| 24 | 33.10 | 41.44 |
| 30 | 20.93 | 28.40 |
| 36 | 10.14 | 14.88 |
| 48 | 2.52 | 4.00 |

The ratio of the area under the curve between Example 25 and Cardizem CD 240 mg. was 1.16:1. The ratio of the average Cmax between Example 25 and Cardizem CD. 240 mg. was 1.26:1.

Outcome

Figure 12:
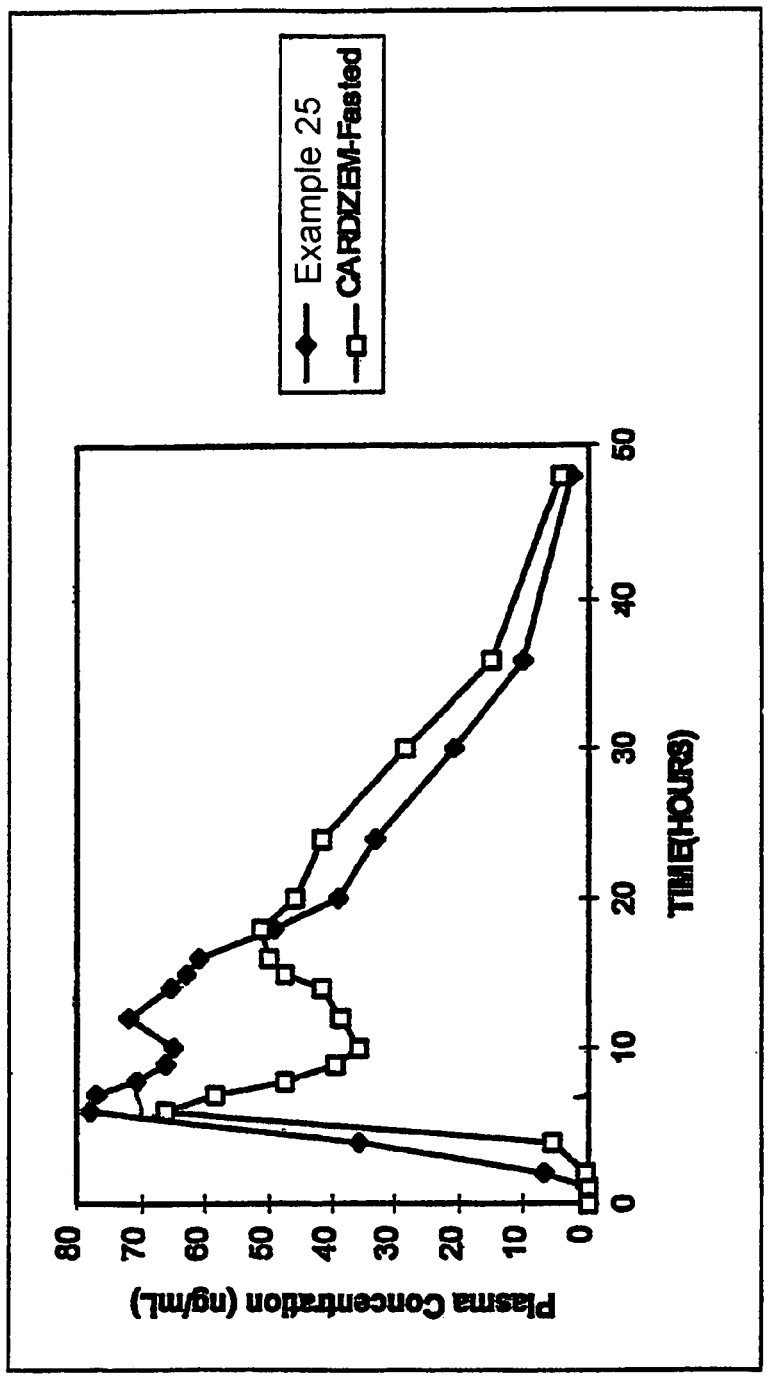
FIG. 12 is a graphical representation of the mean plasma diltiazem concentration (ng/ml) over time for Examples 25 and for a reference standard (Cardizem CD 240 mg).

FIG. 12 and Example 25 demonstrated a Bi-Modal plasma level in-vivo, CARDIZEM CD® also demonstrated Bi-Modal plasma levels by the mixture of two differently processed bead formulations.

Examples 26 AND 27

Effect of Different Excipients

In Examples 26 and 27, a sustained release excipient is prepared in accordance with the procedure set froth in Examples 1 and 3. The ingredients of the sustained release excipient of Examples 25 and 26 are set forth in Table 32 below:

TABLE 32

| | Component (%) | Example 26 | Example 27 |
|---|---|---|---|
| 1. | Xanthan Gum | 12 | 25 |
| 2. | Locust Bean Gum | 18 | 25 |
| 3. | Calcium Sulfate | N/A | 10 |
| 4. | Ethyl Cellulose | N/A | 5 |
| 5. | Dextrose | 70 | 35 |
| 6. | Water* | 25 | N/A |
| 7. | Ethanol* | N/A | 20 |

*Removed during processing

Formulation Table 33

Thereafter, diltiazem tablets are prepared as follows:
The desired amount of diltiazem, fumaric acid and the sustained release excipient are placed in a granulator and mixed for 3 minutes at low speed. Water is added over a 2 minute interval while the impeller is running at low speed (additional water and granulation time may be used to form proper granules). The resultant granules are then dried in a fluid bed dryer until LOD is less than %5 and milled with hammer forward at 2000-3000 rpm using screen #0050. The milled granulation is then placed in a V-Blender with sodium lauryl sulfate and blended for 10 minutes. A suitable tableting lubricant. (Pruv®, sodium stearyl fumarate, NF, commercially available from Penwest Pharmaceuticals Co. is added, and the mixture is blended for another 5 minutes. The resultant granulation is then compressed into tablets using a capsule shaped punch. This final mixture is tableted to approximately 750 mg. The ingredients of the tablets of Examples 26 and 27 are set forth in Table 33 below:

TABLE 33

| | Component | Ex. 26 % | Ex. 26 mg/tab | Ex. 27 % | Ex. 27 mg/tab |
|---|---|---|---|---|---|
| 1 | Sustained Release Excipient | 53.3 | 400.0 | 53.3 | 400.0 |
| 2 | Diltiazem HCI | 32.0 | 240.0 | 32.0 | 240.0 |
| 3 | Fumaric Acid | 8.0 | 60.0 | 8.0 | 60.0 |
| 4 | Surfactant (SLS) | 5.3 | 40.0 | 5.3 | 40.0 |
| 5 | Sodium Stearyl Fumarate | 1.3 | 0.0 | 30.0 | 0.0 |
| 6 | *Water | 27.0 | 0.0 | 30.0 | 0.0 |

*Removed during processing

Figure 13:
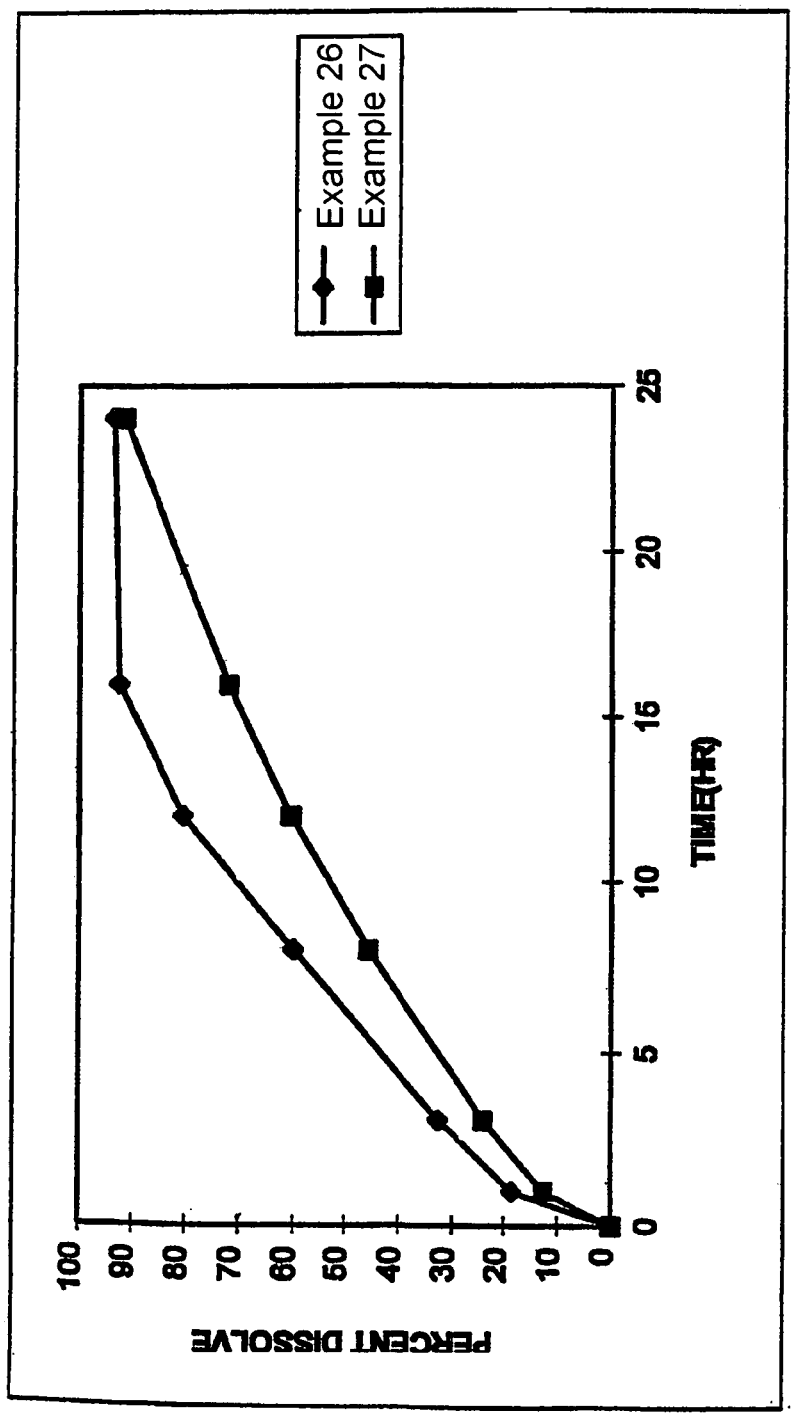
FIG. 13 is a graphical representation of the dissolution (mean percent dissolved over time) for Examples 26 and 27.
Figure 14:
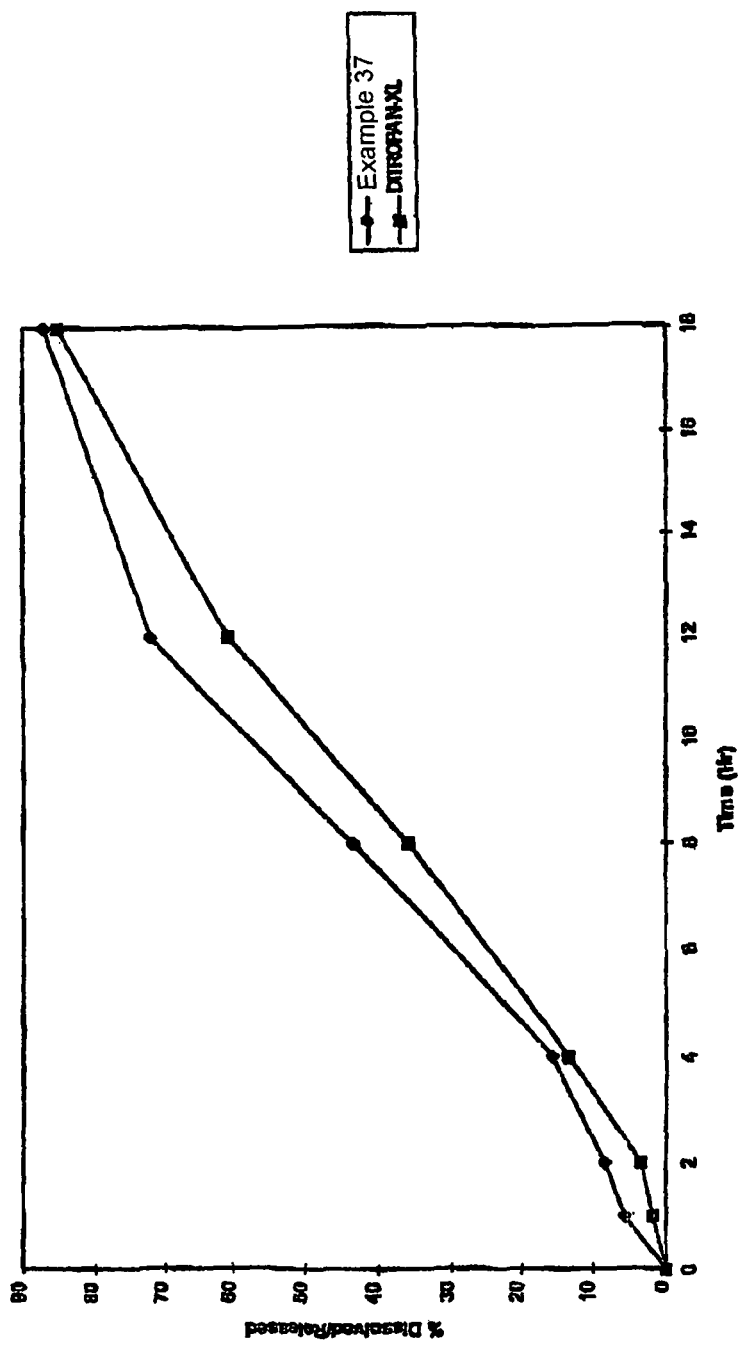
FIG. 14 is a graphical representation comparing the dissolution (mean percent dissolved over time) of Example 37 and for a reference standard (Ditropan XL).

The final tablets in Example 26 have a tablet weight of 750.0 mg. and a hardness of 15 Kp.
The final tablets in Example 27 have a tablet weight of 750.0 mg. and a hardness of 15 Kp.
Dissolution tests were then carried out on the tablets of Example 26 and 27 in 250 ML buffer (pH 6) in an automated USP dissolution apparatus (Paddle type III, 15 CPM), and the amount of drug released was analyzed via UV analysis. The in-vitro are set forth in FIG. 13 and Table 34 below:

TABLE 34

| Time (hours) | Example 25 (% dissolved) | Example 26 (% dissolved) |
|---|---|---|
| 0.0 | 0.0 | 0.0 |
| 1.0 | 18.4 | 12.6 |
| 3.0 | 32.6 | 23.9 |
| 8.0 | 59.8 | 45.9 |
| 12.0 | 80.5 | 60.3 |
| 16.0 | 92.3 | 71.8 |
| 24.0 | 93.7 | 91.4 |

Conclusion

Example 26 had a dissolution profile that was slower than Example 25.

Outcome

Dissolution rate can be modified by using different grades of excipient.

Examples 28-29

Effect of Gum:Drug Ratio in Formulation

In Example 28-29, sustained release excipients in accordance with the present invention are first prepared, the medicament (in this case oxybutynin) and the pH modifying agent (in this case being succinic acid) being added subsequently, and the final mixture then being tableted.

The sustained release excipient is prepared by dispensing xanthan gum, locust bean gum dextrose and calcium sulfate into a high shear mixer/granulator, dispensing ethyl cellulose into a vessel containing ethanol, dispensing the ethyl cellulose/ethanol mixture into the xanthan gum, locust bean gum, dextrose, calcium sulfate mixture and granulating to form proper granules, drying the mixture in a fluid bed dryer and milling the dried material to form proper granules. The ingredients of the sustained-release excipient of Examples 28-29 are set forth in Table 35 below:

TABLE 35

PREPARATION OF SUSTAINED-RELEASE EXCIPIENT

| Component | Amount (%) - Ex. 28 | Amount (%) - Ex. 29 |
|---|---|---|
| 1. Xanthan Gum | 20 | 15 |
| 2. Locust Bean Gum | 30 | 15 |
| 3. Dextrose | 40 | 60 |
| 4. Calcium Sulfate | 10 | 10 |
| 5. Water* | 20-30 | 20-30 |

*Removed during processing.

Next, the desired amount of oxybutynin and sodium stearyl fumarate are screened through a 25 mesh sieve, the screened oxybutynin and sustained release excipient are dispensed into a V-blender and blended for 10 minutes, the screened sodium stearyl fumarate is added into the blended mixture of oxybutynin and sustained-release excipient and blended for an additional 5 minutes, the final blended end product is then compressed into tablets using a 5/16" round shaped tooling. This final mixture is tableted to approximately 179.4 mg. The ingredients of the tablets of Examples 28-29 are set forth in Tables 36 and 37 below:

TABLE 36

TABLET FORMULATION - EXAMPLE 28

| | Component | Amount (%) | Amount (mg/tab) |
|---|---|---|---|
| 1. | Sustained Release Excipient | 92.9 | 166.7 |
| 2. | Oxybutynin HCL | 5.6 | 10.0 |
| 3. | Sodium Stearyl Fumarate | 1.5 | 2.7 |
| Tablet weight | | | 179.4 |
| Hardness (Kp) | | | 5 |

TABLE 37

TABLET FORMULATION - EXAMPLE 29

| | Component | Amount (%) | Amount (mg/tab) |
|---|---|---|---|
| 1. | Sustained Release Excipient | 92.9 | 166.7 |
| 2. | Oxybutynin HCL | 5.6 | 10.0 |
| 3. | Sodium Stearyl Fumarate | 1.5 | 2.7 |
| Tablet weight | | | 179.4 |
| Hardness (Kp) | | | 5 |

The final tablets have a tablet weight of 179.4.0 mg and a hardness of 5 Kp.

Dissolution tests were then carried out on the tablets of Examples 28-29. The in-vitro dissolution results are set forth in Table 38 below.

TABLE 38

| Time (hr) | Ex. 28 (% dissolved) | Ex. 29 (% dissolved) |
|---|---|---|
| 0.0 | 0.0 | 0.0 |
| 2.0 | 44.4 | 33.6 |
| 4.0 | 67.6 | 42.5 |
| 6.0 | 86.6 | 57.4 |
| 8.0 | 103.0 | 72.5 |
| 12.0 | 108.7 | 88.9 |
| 20.0 | 108.7 | 92.8 |

The formulation of Example 28 has a drug:gum ratio of 1:5 and the formulation of Example 29 has a drug:gum ratio of 1:8.3. From the results provided in Table 38, it is evident that the rate of release of oxybutynin is slower as the drug:gum ratio in the formulations is increased.

Examples 30-31

Effect of Gum:Dextrose Ratio

In Examples 30-31, a sustained release excipient is prepared in accordance with the procedure set forth in Examples 28 and 29. The ingredients of the sustained release excipient of Examples 30 and 31 are set forth in Table 39 below:

TABLE 39

| | Component | Amount (%) Ex. 30 | Amount (%) Ex. 31 |
|---|---|---|---|
| 1 | Xanthan Gum | 20 | 15 |
| 2 | Locust Bean Gum | 30 | 15 |
| 3 | Dextrose | 40 | 60 |
| 4 | Calcium Sulfate | 10 | 10 |
| 5 | Water* | 20-30 | 20-30 |

*Removed during processing

Thereafter, oxybutynin tablets are prepared as follows:

The desired amount of oxybutynin and sodium stearyl fumarate are screened through a 25 mesh sieve, the screened oxybutynin and sustained release excipient are dispensed into a V-blender and blended for 10 minutes, the screened sodium stearyl fumarate is added into the blended mixture of oxybutynin and sustained-release excipient and blended for an additional 5 minutes, the final blended end product is then compressed into tablets using a 5/16" round shaped tooling. This final mixture is tableted to approximately 179.4 mg. The ingredients of the tablets of Examples 30-31 are set forth in Tables 40 and 41 below:

TABLE 40

TABLET FORMULATION - EXAMPLE 30

| | Component | Amount (%) | Amount (mg/tab) |
|---|---|---|---|
| 1. | Sustained Release Excipient | 92.9 | 166.7 |
| 2. | Oxybutynin HCL | 5.6 | 10.0 |
| 3. | Sodium Stearyl Fumarate | 1.5 | 2.7 |
| Tablet weight | | | 179.4 |
| Hardness (Kp) | | | 5 |

TABLE 41

TABLET FORMULATION - EXAMPLE 31

| | Component | Amount (%) | Amount (mg/tab) |
|---|---|---|---|
| 1. | Sustained Release Excipient | 92.9 | 166.7 |
| 2. | Oxybutynin HCL | 5.6 | 10.0 |
| 3. | Sodium Stearyl Fumarate | 1.5 | 2.7 |
| Tablet weight | | | 179.4 |
| Hardness (Kp) | | | 5 |

The final tablets have a tablet weight of 17940 mg and a hardness of 5 Kp.

Dissolution tests were then carried out on the tablets of Examples 30-31. The in-vitro dissolution results are set forth in Table 38 below.

TABLE 42

| Time (hr) | Ex. 30 (% dissolved) | Ex. 31 (% dissolved) |
|---|---|---|
| 0.0 | 0.0 | 0.0 |
| 2.0 | 44.4 | 33.6 |
| 4.0 | 67.6 | 42.5 |
| 6.0 | 86.6 | 57.4 |
| 8.0 | 103.0 | 72.5 |
| 12.0 | 108.7 | 88.9 |
| 20.0 | 108.7 | 92.8 |

From the results provided in Table 42, it is evident that as the amount of gum relative to the amount of dextrose is increased, a corresponding decrease in release of oxybutynin is observed.

Examples 32-35

Effect of Succinic Acid

In Examples 32-33, a sustained release excipient is prepared in accordance with the procedure set forth in Examples 28 and 29. The ingredients of the sustained release excipient of Examples 32 and 33 are set forth in Table 43 below:

TABLE 43

| | Component | Amount (%) - Ex. 32-33 |
|---|---|---|
| 1 | Xanthan Gum | 25 |
| 2 | Locust Bean Gum | 25 |
| 3 | Dextrose | 35 |
| 4 | Calcium Sulfate | 10 |
| 5 | Ethyl Cellulose | 5 |
| 6 | Water* | 20-30 |

*Removed during processing

Thereafter, oxybutynin tablets are prepared as follows:

The desired amount of succinic acid, oxybutynin and sodium stearyl fumarate are screened through a 25 mesh sieve, the screened succinic acid and sustained release excipient are dispensed into a V-blender and blended for 10 minutes, the screened oxybutynin is added into the blended mixture of succinic acid and sustained-release excipient and blended for an additional 5 minutes, the screened sodium stearyl fumarate is added to the blended mixture of oxybutynin, succinic acid and sustained-release excipient and blended for an additional 5 minutes, the final blended end product is then compressed into tablets using a 5/16" round shaped tooling. The final mixture of Example 32 is tableted to approximately 251.0 mg and the final mixture of Example 33 is tableted to approximately 296.0 mg. The ingredients in Examples 32-33 are set forth in Tables 44 and 45 below:

TABLE 44

TABLET FORMULATION - EXAMPLE 32

| | Component | Amount (%) | Amount (mg/tab) |
|---|---|---|---|
| 1. | Sustained Release Excipient | 93.2 | 234.0 |
| 2. | Succinic Acid | N/A | N/A |
| 3. | Oxybutynin HCL | 6 | 15.0 |
| 4. | Sodium Stearyl Fumarate | 0.8 | 2.0 |
| Tablet weight | | | 251 |
| Hardness (Kp) | | | 8 |

The final tablets have a tablet weight of 251.0 mg and a hardness of 8 Kp.

TABLE 45

TABLET FORMULATION - EXAMPLE 33

| | Component | Amount (%) | Amount (mg/tab) |
|---|---|---|---|
| 1. | Sustained Release Excipient | 92.9 | 166.7 |
| 2. | Succinic Acid | 15.2 | 45.0 |
| 2. | Oxybutynin HCL | 5.1 | 15.0 |
| 3. | Sodium Stearyl Fumarate | 0.7 | 2.0 |
| Tablet weight | | | 296.0 |
| Hardness (Kp) | | | 8 |

The final tablets have a tablet weight of 296.0 mg and a hardness of 8 Kp.

Dissolution tests were then carried out on the tablets of Examples 32-33. The in-vitro dissolution results are set forth in Table 46 below:

TABLE 46

| Time (hr) | Ex. 32 (% dissolved) (0%) | Ex. 33 (% dissolved) (15%) |
|---|---|---|
| 0.0 | 0.0 | 0.0 |
| 2.0 | 1.3 | 8.9 |
| 4.0 | 2.1 | 12.9 |
| 6.0 | 4.7 | 24.0 |
| 8.0 | 11.3 | 34.0 |
| 12.0 | 25.9 | 44.0 |
| 20.0 | 43.9 | 59.5 |

From the results provided in Table 46, it is evident that the addition of Succinic Acid aids in the solubility of the drug substance, therefore, increasing the release rate.

In Examples 34-35, a sustained release excipient is prepared in accordance with the procedure set forth in Examples 28 and 29. The ingredients of the sustained release excipient of Examples 34 and 35 are set forth in Table 47 below:

TABLE 47

| | Component | Amount (%) - Ex. 34-35 |
|---|---|---|
| 1 | Xanthan Gum | 25 |
| 2 | Locust Bean Gum | 25 |
| 3 | Dextrose | 35 |
| 4 | Calcium Sulfate | 10 |
| 5 | Ethyl Cellulose | 5 |
| 6 | Water* | 20-30 |

*Removed during processing

Thereafter, oxybutynin tablets are prepared as follows:

The desired amount of sustained-release excipient, succinic acid, and oxybutynin are dispensed into a granulator. They are dry mixed for 3 minutes with the impeller at low speed with the chopper blade in the off position. Water is added over a 1 minute interval, then the mixture is granulated at high speed for 3 minutes (additional water and granulation time may be used to form proper granules). Next, the mixture is dried in a fluid bed dryer until the LOD is less than 5%. The dried granulation is milled with the blade forward at 2000-3000 rpm. The milled granulation and sodium stearyl fumarate are placed into a V-Blender and blended for 10 minutes. The blended mixture is then compressed into tablets using a 5/16" round shaped tooling. The final mixture of Example 34 is tableted to approximately 296.0 mg and the final mixture of Example 35 is tableted to approximately 266.0 mg. The ingredients in Examples 34-35 are set forth in Tables 48 and 49 below:

TABLE 48

TABLET FORMULATION - EXAMPLE 34

| | Component | Amount (%) | Amount (mg/tab) |
|---|---|---|---|
| 1. | Sustained Release Excipient | 79.1 | 234.0 |
| 2. | Succinic Acid | 15.2 | 45.0 |
| 3. | Oxybutynin HCL | 5.1 | 15.0 |
| 4. | Sodium Stearyl Fumarate | 0.7 | 2.0 |
| 5. | Water* | 30-45 | N/A |
| Tablet weight | | | 296.0 |
| Hardness (Kp) | | | 8 |

*Removed during processing

The final tablets have a tablet weight of 296.0.0 mg and a hardness of 8 Kp.

TABLE 49

TABLET FORMULATION - EXAMPLE 35

| | Component | Amount (%) | Amount (mg/tab) |
|---|---|---|---|
| 1. | Sustained Release Excipient | 88.0 | 234.0 |
| 2. | Succinic Acid | 5.6 | 15.0 |
| 3. | Oxybutynin HCL | 5.6 | 15.0 |
| 4. | Sodium Stearyl Fumarate | 0.8 | 2.0 |
| 5. | Water* | 30-45 | N/A |
| Tablet weight | | | 266.0 |
| Hardness (Kp) | | | 8 |

*Removed during processing

The final tablets have a tablet weight of 266.0 mg and a hardness of 8 Kp.

Dissolution tests were then carried out on the tablets of Examples 34-35. The in-vitro dissolution results are set forth in Table 50 below:

TABLE 50

| Time (hr) | Ex. 32 (% dissolved) (15%) | Ex. 33 (% dissolved) (6%) |
|---|---|---|
| 0.0 | 0.0 | 0.0 |
| 2.0 | 9.2 | 5.8 |
| 4.0 | 13.7 | 7.9 |
| 6.0 | 21.2 | 11.7 |
| 8.0 | 34.2 | 23.4 |
| 12.0 | 49.1 | 37.4 |
| 18.0 | 63.9 | 57.5 |

From the results provided in Table 50, it is evident that the higher the amount of Succinic Acid in the formulation the faster the release rate.

Example 36

Effect of Coating Tablets with Ethylcellulose (SURELEASE®)/OPADRY® (80/20) Aqueous Dispersion

The procedure for preparing the Ethylcellulose/Opadry® coating is as follows:

First, weigh 340 g of Water in a suitable container, add 60 g of Opadry® to the water while mixing. Continue to mix. While mixing the Opadry® dispersion, add 933 g of Ethylcellulose dispersion (Surelease®) and allow to stir for 30-60 minutes. The final dispersion is used to coat the tablets for a weight gain of 3-5% based on the whole weight of the tablet.

In Example 36, a sustained release excipient is prepared in accordance with the procedure set forth in Examples 28 and 29. The ingredients of the sustained release excipient of Example 36 is set forth in Table 51 below:

TABLE 51

| | Component | Amount (%) - Ex. 36 |
|---|---|---|
| 1. | Xanthan Gum | 25 |
| 2 | Locust Bean Gum | 25 |
| 3 | Dextrose | 35 |
| 4 | Calcium Sulfate | 10 |
| 5 | Ethyl Cellulose | 5 |
| 6 | Water* | 20-30 |

*Removed during processing

Thereafter, oxybutynin tablets are prepared as follows:

The desired amount of sustained-release excipient, succinic acid, and oxybutynin are dispensed into a granulator. They are dry mixed for 3 minutes with the impeller at low speed with the chopper blade in the off position. Water is added over a 1 minute interval, then the mixture is granulated at high speed for 3 minutes (additional water and granulation time may be used to form proper granules). Next, the mixture is dried in a fluid bed dryer until the LOD is less than 5%. The dried granulation is milled with the blade forward at 2000-3000 rpm. The milled granulation and sodium stearyl fumarate are placed into a V-Blender and blended for 10 minutes. The blended mixture is then compressed into tablets using a 5/16" round shaped tooling. The final mixture of Example 36 is tableted to approximately 296.0 mg. The ingredients in Examples 36 is set forth in Table 52 below:

TABLE 52

TABLET FORMULATION - EXAMPLE 36

| | Component | Amount (%) | Amount (mg/tab) |
|---|---|---|---|
| 1. | Sustained Release Excipient | 79.1 | 234.0 |
| 2. | Succinic Acid | 15.2 | 45.0 |
| 3. | Oxybutynin HCL | 5.1 | 15.0 |
| 4. | Sodium Stearyl Fumarate | 0.7 | 2.0 |
| 5. | Water* | 30-45 | N/A |
| Tablet weight | | | 296.0 |
| Hardness (Kp) | | | 8 |

*Removed during processing

The final tablets have a tablet weight of 296.0.0 mg and a hardness of 8 Kp.

Dissolution tests were then carried out on the tablets of Example 36. The in-vitro dissolution results are set forth in Table 53 below:

TABLE 53

| Time (hr) | Ex. 1 | Ex. 2 | Ex. 3 |
|---|---|---|---|
| 0.0 | 0.0 | 0.0 | 0.0 |
| 2.0 | 26.8 | 7.1 | 1.7 |
| 4.0 | 32.1 | 10.3 | 2.8 |
| 6.0 | 35.8 | 14.9 | 5.5 |
| 8.0 | 40.1 | 20.2 | 9.0 |
| 12.0 | 54.2 | 27.4 | 15.1 |
| 20.0 | 72.2 | 53.2 | 32.7 |

From the results provided in Table 53, it is evident that as the amount, by weight of coating increased, the release rate decreased.

Example 37

Effect of Fumaric Acid

In Example 37, a sustained-release excipient is prepared in accordance with the procedure set forth in Examples 28-29. The ingredients of the sustained-release excipient of Example 37 is set forth in Table 54 below:

TABLE 54

|   | Component | Amount (%) - Ex. 37 |
|---|---|---|
| 1 | Xanthan Gum | 25 |
| 2 | Locust Bean Gum | 25 |
| 3 | Dextrose | 35 |
| 4 | Calcium Sulfate | 10 |
| 5 | Ethyl Cellulose | 5 |
| 6 | Water* | 20-30 |

*Removed during processing

TABLET FORMULATION - EXAMPLE 37

|   | Component | Amount (mg/tab) |
|---|---|---|
| 1. | Sustained Release Excipient | 166.7 |
| 2. | Oxybutynin HCL | 15 |
| 3. | Fumaric Acid | 30 |
| 4. | Pruv ® | 2 |
|   | Total (core only) | 213.7 |

The final tablets have a tablet weight of 213.7 mg.

Dissolution tests were then carried out on the tablets of Example 37 in comparison to Ditropan XL. The in-vitro dissolution results are set forth in Table 55 below:

TABLE 55

| | % Dissolved/Released | |
|---|---|---|
| Time (hr) | Ditropan XL | 149-141 |
| 0 | 0 | 0 |
| 1 | 1.9 | 5.9 |
| 2 | 3.5 | 8.5 |
| 4 | 13.4 | 15.7 |
| 8 | 36.1 | 43.50 |
| 12 | 60.7 | 72.1 |
| 18 | 85.0 | 86.9 |
| Recovery | 98.4 | 98.0 |

Other formulations of Oxybutynin wherein the pH modifying agent comprises fumaric acid are set forth in Table 56 below:

TABLE 56

|   | Component | mg/tab (range) or % as noted |
|---|---|---|
| 1. | Sustained Release Excipient | 170-234 mg |
| 2. | Fumaric Acid | 15-60 mg |
| 3. | Oxybutynin HCL | 5, 10, 15 mg |
| 4. | Silicon Dioxide | 0-2% |
| 5. | Sodium Stearyl Fumarate | 1-2% |

The examples provided above are not meant to be exclusive. Many other variations of the present invention would be obvious to those skilled in the art, and are contemplated to be within the scope of the appended claims.

What is claimed is:

1. A sustained release oral tablet comprising a sustained release matrix comprising:
a therapeutically effective amount of a medicament having an aqueous solubility of more than 10 g/1;
a pH modifying agent which is an organic acid;
a sustained release excipient comprising a gelling agent, an inert pharmaceutical diluent selected from the group consisting of monosaccharide, a disaccharide, a polyhydric alcohol, and mixtures thereof, said gelling agent comprising a Xanthan gum and a locust bean gum capable of cross-linking said Xanthan gum when exposed to an environmental fluid, the sustained release excipient further comprising an optional surfactant selected from the group consisting of monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates, ethoxylated alkyl sulfates, ester linked sulfonates, alpha olefin sulfonates, phosphated ethoxylated alcohols, monoalkyl quaternary ammonium salts, dialkyl quaternary ammonium compounds, amidoamines, aminimides, N-substituted alkyl amides, N-alkyl betaines, sulfobetaines, and N-alkyl β-aminoproprionates, an ester of polyethyleneglycol, an ether of polyethyleneglycol, and mixtures of any of the foregoing, and an optional ionizable gel strength enhancing agent selected from the group consisting of an alkali metal sulfate, an alkali metal chloride, an alkali metal chloride, an alkali metal borate, an alkali metal bromide, an alkali metal citrate, an alkali metal acetate, an alkali metal lactate, an alkaline earth metal sulfate, an alkaline earth metal chloride, an alkaline earth metal chloride, an alkaline earth metal borate, an alkaline earth metal bromide, an alkaline earth metal citrate, an alkaline earth metal acetate, an alkaline earth metal lactate, and mixtures of any of the foregoing; the ingredients of the sustained release excipient being granulated together prior to incorporation of the medicament; the medicament being incorporated into the sustained release matrix together with the sustained release excipient and the pH modifying agent such that said tablet provides a sustained release of said medicament after oral administration to human patients for at least about 12 hours or at least about 24 hours, the tablet having a total weight from about 300 mg to about 1000 mg, and wherein the medicament is on oxybutynin.

2. The sustained release oral tablet of claim 1 which provides a sustained release of said medicament for at least about 12 hours after oral administration.

3. The sustained release oral tablet of claim 1 which provides a sustained release of said medicament for at least about 24 hours after oral administration.

4. The sustained release oral tablet of claim 1, wherein said medicament has an aqueous solubility of more than about 100 g/l.

5. The sustained release oral tablet of claim 1, wherein said medicament has an aqueous solubility of more than about 1000 g/l.

6. The sustained release oral tablet of claim 1, wherein the ratio of said inert diluent to said gelling agent is from about 1:3 to about 3:1.

7. The sustained release oral tablet of claim 1, wherein the ratio of said medicament to said gelling agent is from about 1:5 to about 5:1.

8. The sustained release oral tablet of claim 1, further comprising an ionizable gel strength enhancing agent.

9. The sustained release oral tablet of claim 8, wherein said ionizable gel strength enhancing agent comprises calcium sulfate.

10. The sustained release oral tablet of claim 1, wherein said organic acid is selected from the group consisting of citric acid, succinic acid, fumaric acid, malic acid, maleic acid, glutaric acid, lactic acid and combinations thereof.

11. The sustained release oral tablet of claim 10, wherein said organic acid is fumaric acid.

12. The sustained release oral tablet of claim 1, wherein said pH modifying agent is present in an amount from about 1% to about 10%.

13. The sustained release oral tablet of claim 1, further comprising a surfactant.

14. The sustained release oral tablet of claim 13, wherein said surfactant is selected from the group consisting of sodium lauryl sulfate and a pharmaceutically effective salt of docusate.

15. The sustained release oral tablet of claim 1, wherein the sustained release excipient further comprises from about 1 to about 20% by weight of a hydrophobic material.

16. The sustained release oral tablet of claim 15, wherein the hydrophobic material is selected from the group consisting of an alkylcellulose, a copolymer of acrylic and methacrylic acid esters, waxes, shellac, zein, hydrogenated vegetable oil, and mixtures thereof, in an amount effective to slow the hydration of the gelling agent when exposed to an environmental fluid.

17. The sustained release oral tablet of claim 1, wherein the medicament is selected from the group consisting of azatadine maleate, brompheniramine maleate, carbinoxamine maleate, chlorpheniramine maleate, dexchlorpheniramine maleate, diphenhydramine hydrochloride, doxylamine succinate, methdilazine hydrochloride, promethazine, trimeprazine tartrate, tripelennamine citrate, tripelennamine hydrochloride, triprolidine hydrochloride, penicillin v potassium, cloxacillin sodium, dicloxacillin sodium, nafcillin sodium, oxacillin sodium, carbenicillin indanyl sodium, oxytetracycline hydrochloride, tetracycline hydrochloride, clindamycin phosphate, clindamycin hydrochloride, clindamycin palmitate HCl, lincomycin HCl, novobiocin sodium, nitrofurantoin sodium, metronidazole hydrochloride, isoniazid, ambenonium chloride, bethanecol chloride, neostigmine bromide, pyridostigmine bromide, anisotropine methylbromide, clidinium bromide, dicyclomine hydrochloride, glycopyrrolate, hexocyclium methylsulfate, homatropine methylbromide, hyoscyamine sulphate, methanthehne bromide, hyoscine hydrobromide, oxyphenonium bromide, propantheline bromide, tridihexethyl chloride, bitolterol mesylate, ephedrine, ephedrine hydrochloride, ephedrine sulphate, orciprenaline sulphate, phenylpropanolamine hydrochloride, pseudoephedrine hydrochloride, ritodrine hydrochloride, salbutamol sulphate, terbutaline sulphate, phenoxybenzamine hydrochloride, ferrous gluconate, ferrous sulphate, anuinocaproic acid, acebutolol hydrochloride, disopyramide phosphate, flecamide acetate, procainamide hydrochloride, propranolol hydrochloride, quinidine gluconate, timolol maleate, tocamide hydrochloride, verapamil hydrochloride, captopril, clonidine hydrochloride, hydralazine hydrochloride; mecamylamine hydrochloride, metoprolol tartrate, papaverine hydrochloride, choline salicylate, magnesium salicylate, meclofenamate sodium, naproxen sodium, tolnetin sodium, phenobarbital sodium, phenyloin sodium, troxidone, ethosuximide, valproate sodium, acetophenazine maleate, chlorpromazine hydrochloride, fluphenazine hydrochloride, prochlorperazine edisylate, promethazine hydrochloride, thioridazine hydrochloride, trifluoroperazine hydrochloride, lithium citrate, molindone hydrochloride, thiothixine hydrochloride, benzamphetamine hydrochloride, dextroamphetamine sulphate, dextroamphetamine phosphate, diethylpropion hydrochloride, fenfluramine hydrochloride, methamphetamine hydrochloride, methylphenidate hydrochloride, phendimetrazine tartrate, phenmetrazine hydrochloride, caffeine citrate, amylobarbital sodium, butabarbital sodium, secobarbital sodium, hydroxyzine hydrochloride, methprylon, potassium iodide, benzaquinamide hydrochloride, metoclopropamide hydrochloride, trimethobenzamide hydrochloride, ranitidine hydrochloride, penicillamine, penicillamine hydrochloride, methimazole, flavoxate hydrochloride, thiamine hydrochloride, ascorbic acids, amantadine hydrochloride, colchicine, etidronate disodium, leucovorin calcium, methylene blue, potassium chloride, and pralidoxime chloride.

18. The sustained release oral tablet of claim 1, wherein the ratio of medicament to gelling agent is from about 1.25:1 to about 2:1.

19. A sustained release oral tablet comprising a sustained release matrix comprising:
 a therapeutically effective amount of a medicament having an aqueous solubility of more than 10 g/l;
 a pH modifying agent in an amount from about 1% to about 10% of the tablet, which is an organic acid selected from the group consisting of citric acid, succinic acid, fumaric acid, malic acid, maleic acid, glutaric acid, lactic acid and combinations thereof;
 a sustained release excipient comprising a gelling agent, an inert pharmaceutical diluent selected from the group consisting of monosaccharide, a disaccharide, a polyhydric alcohol, and mixtures thereof, said gelling agent comprising xanthan gum and locust bean gum in a ratio of about 1:1.5, the sustained release excipient further comprising an optional surfactant selected from the group consisting of monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates, ethoxylated alkyl sulfates, ester linked sulfonates, alpha olefin sulfonates, phosphated ethoxylated alcohols, monoalkyl quaternary ammonium salts, dialkyl quaternary ammonium compounds, amidoamines, aminimides, N-substituted alkyl amides, N-alkyl betaines, sulfobetaines, and N-alkyl B-aminoproprionates, an ester of polyethyleneglycol, an ether of polyethyleneglycol, and mixtures of any of the foregoing, and an optional ionizable gel strength enhancing agent selected from the group consisting of an alkali metal sulfate, an alkali metal chloride, an alkali metal chloride, an alkali metal borate, an alkali metal bromide, an alkali metal citrate, an alkali metal acetate, an alkali metal lactate, an alkaline earth metal sulfate, an alkaline earth metal chloride, an alkaline earth metal chloride, an alkaline earth metal borate, an alkaline earth metal bromide, an alkaline earth metal citrate, an alkaline earth metal acetate, an alkaline earth metal lactate, and mixtures of any of the foregoing; the ingredients of the sustained release excipient being granulated together prior to incorporation of the medicament;
 and the medicament being incorporated into the sustained release matrix together with the sustained release excipient and the pH modifying agent such that said tablet provides a sustained release of said medicament after oral administration to human patients such when orally administered to a human patient, the sustained release oral tablet provides therapeutic blood levels for about 12 or about 24 hours, the tablet having a total weight from about 300 mg to about 1000 mg, and wherein the medicament is not oxybutynin.

* * * * *